(12) United States Patent
Ong et al.

(10) Patent No.: US 7,319,411 B2
(45) Date of Patent: Jan. 15, 2008

(54) NETWORK OF SENSOR NODES ASSEMBLIES AND METHOD OF REMOTE SENSING WITHIN LIQUID ENVIRONMENTS

(75) Inventors: Keat Ghee Ong, State College, PA (US); Craig A. Grimes, Boalsburg, PA (US)

(73) Assignee: KMG2 Sensors Corporation, Boalsburg, PA (US)

( * ) Notice: Subject to any disclaimer, the term of this patent is extended or adjusted under 35 U.S.C. 154(b) by 895 days.

(21) Appl. No.: 10/622,244

(22) Filed: Jul. 18, 2003

(65) Prior Publication Data

US 2004/0066313 A1    Apr. 8, 2004

Related U.S. Application Data

(60) Provisional application No. 60/397,176, filed on Jul. 18, 2002.

(51) Int. Cl.
*G08C 17/00* (2006.01)

(52) U.S. Cl. .................. 340/870.11; 367/134

(58) Field of Classification Search ............ 367/134, 367/131; 340/825.37, 825.69, 984; 342/23
See application file for complete search history.

(56) References Cited

U.S. PATENT DOCUMENTS

| | | | | |
|---|---|---|---|---|
| 5,303,207 | A * | 4/1994 | Brady et al. | 367/134 |
| 5,896,412 | A | 4/1999 | Levanon et al. | 375/202 |
| 6,393,921 | B1 | 5/2002 | Grimes et al. | 73/728 |
| 6,397,661 | B1 | 6/2002 | Grimes et al. | 73/24.06 |
| 2002/0020533 | A1* | 2/2002 | Tubel | 166/313 |

OTHER PUBLICATIONS

Reindl et al. "Theory and Application of Passive SAW Radio Transponders as Sensors," *IEEE Transactions on Ultrasonics, Ferroelectrics, and Frequency Control*, vol. 45, No. 5, (Sep. 1998); {labeled "ATTACHMENT B" of provisional app. filed Jul. 18, 2002}.

(Continued)

*Primary Examiner*—Brian Zimmerman
*Assistant Examiner*—Hung Q Dang
(74) *Attorney, Agent, or Firm*—Macheledt, Bales & Heidmiller LLP

(57) ABSTRACT

A network of remote sensing node assemblies, a first and second of which each has a sensor element, as well as associated technique and program code for transmitting information collected about a liquid environment. The network provides the capability of sensing the liquid to collect a wide variety of types of information/data about the liquid and any surrounding environments, and transmitting from the originating node assembly to a different node within acoustic transmission range, and then transmitting further to a third node assembly where the information may be processed and communicated to a user, or further transmitted by way of suitable medium, preferably as electromagnetic signals, to a host location for processing into a compilation of data. Each of at least two sensing node assemblies has at least one sensor element adapted for operation while immersed within the liquid, a source of power, and a transducer for receiving acoustic waves/signals transmitted from another node assembly. The transducer is adapted for emitting sensor information collected by one or more sensor element(s) at that node, as well as acting as a pass-through node for information collected at other nodes. A third node assembly of the network is adapted for receiving and processing sensor information acoustically transmitted from other nodes. The third node can have its own processor unit(s) and means for transmitting sensor information to a remote host, whether originating at the third node (if so equipped) or another node assembly.

10 Claims, 9 Drawing Sheets

OTHER PUBLICATIONS

Frye et al. "Optimizing Surface Acoustic Wave Sensors for Trace Chemical Detection," *IEEE International Conference on Solid-state Sensors and Actuators*, (1997) 1323-1326 {labeled "ATTACHMENT C" of provisional app. filed Jul. 18, 2002}.

Grimes, C.A., K.G. Ong, et al. "Magnetoelastic sensors for remote query environmental monitoring," *Journal of Smart Materials and Structures*, vol. 8 (1999) 639-646; {labeled "ATTACHMENT D" of provisional app. filed Jul. 18, 2002}.

Jain, M.K., C. A. Grimes, "A Wireless Magnetoelastic Micro-Sensor Array for Simultaneous Measurement of Temperature and Pressure," *IEEE Transactions on Magnetics*, vol. 37, No. 4, pp. 2022-2024, 2001; {labeled "ATTACHMENT E" of provisional app. filed Jul. 18, 2002}.

M. Rodriguez, Jr. et al., "Biosensors for rapid monitoring of primary-source drinking water using naturally occurring photosynthesis," *Biosensors and Bioelectronics*, 17 (2002) 843-849.

"Streams Harbor Chemical Potpourri," *Science*, vol. 295, p. 2209, Mar. 22, 2002.

Portions of Ch. 5, "*Modulation and Amplitude-Modulated Systems, et al*" Ch. 11 "*Pulse and Digital Modulation*, et al." Ch. 13 "*Data Communication Techniques*, et al." and Ch. 17 "*Digital Radio and Space Communication*, et al." 3$^{rd}$ Ed., Paul H. Young, Macmillan Pub. Co., earlier versions 1985, 1990, 3$^{rd}$ Ed. 1994.

\* cited by examiner

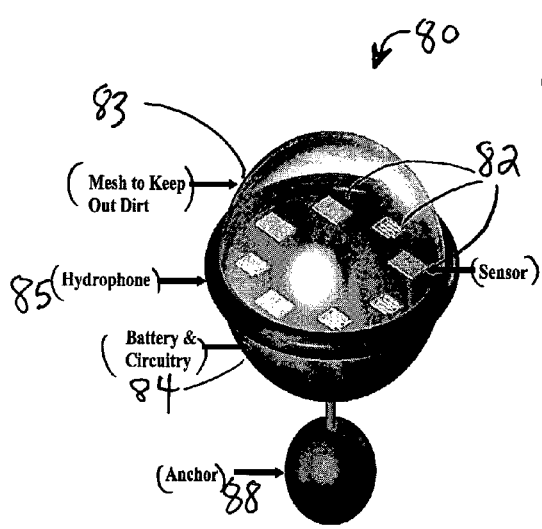
FIG. 4
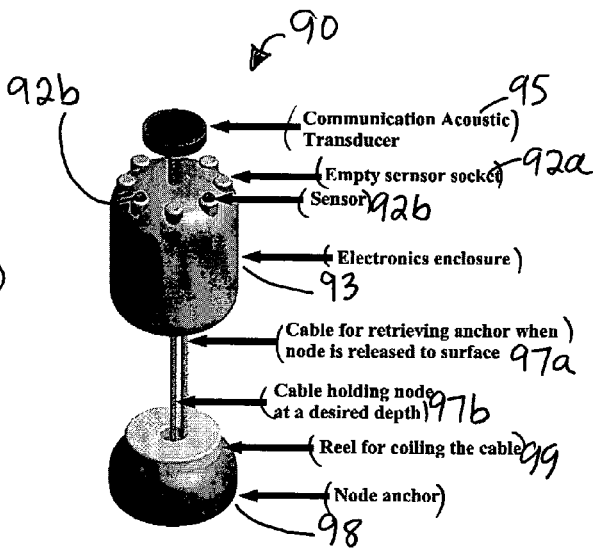
FIG. 5
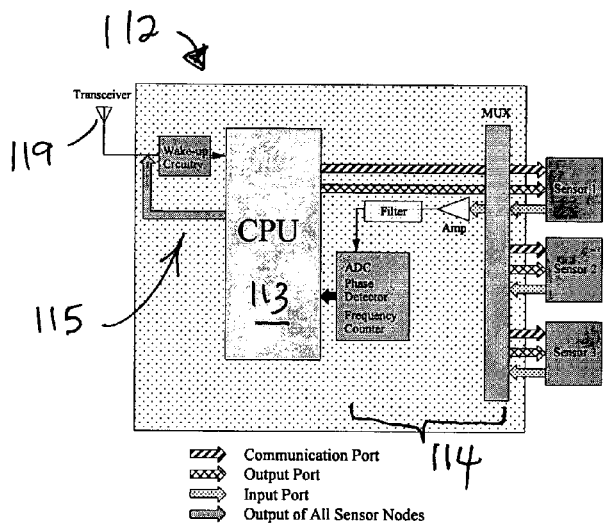
FIG. 6
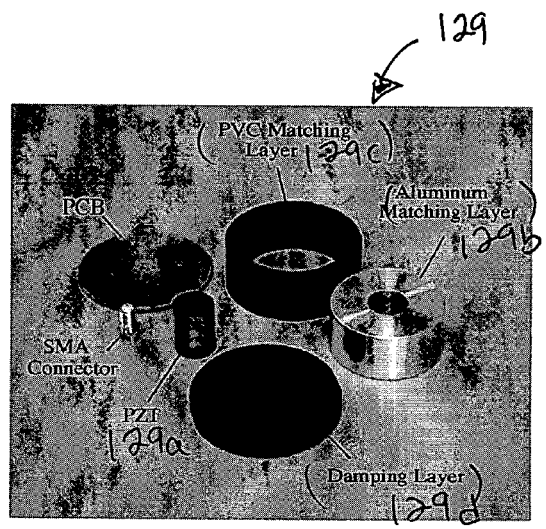
FIG. 7
FIG. 8
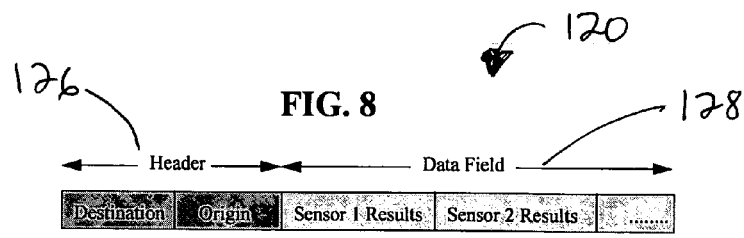

FIG. 9
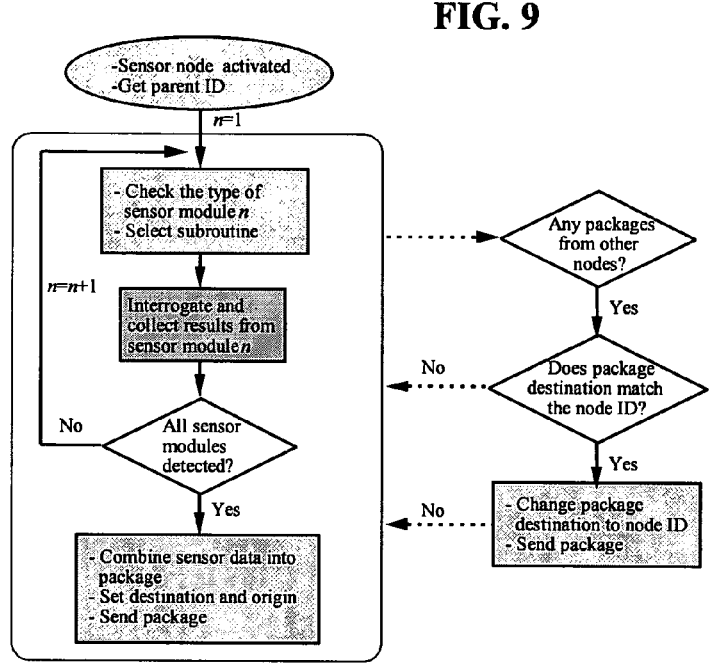
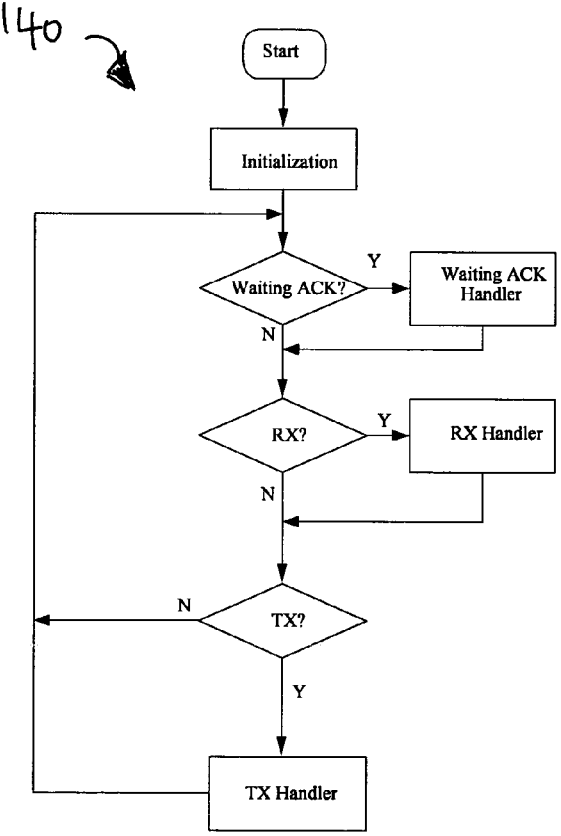
FIG. 10
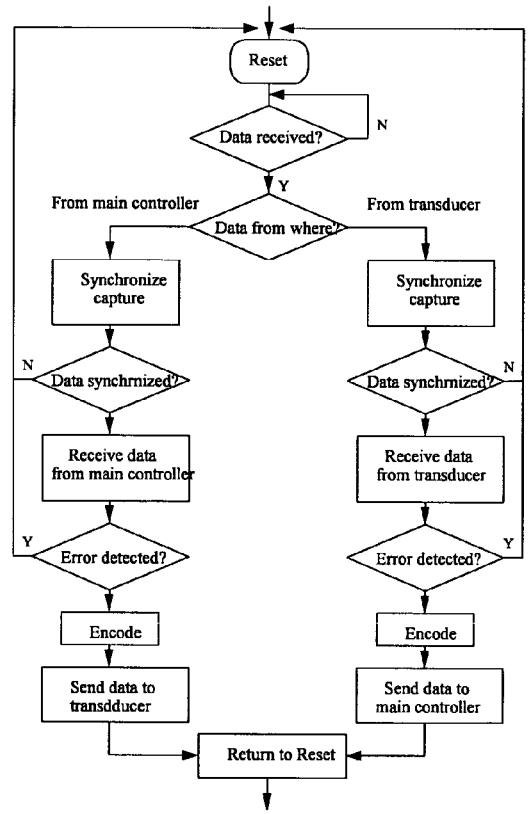
FIG. 11

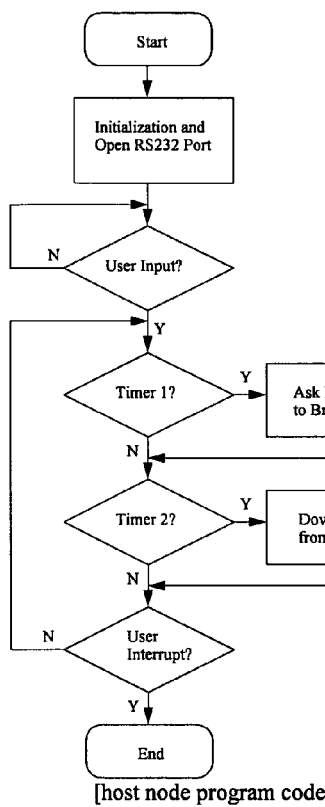
[host node program code]
FIG. 12
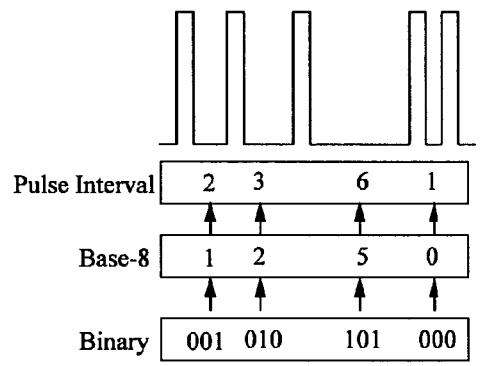
FIG. 14
FIG. 13
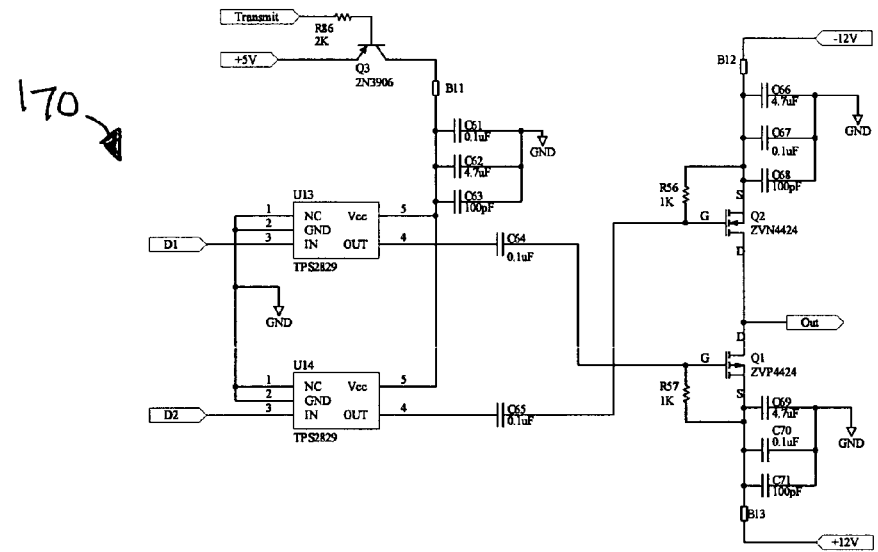
Circuitry to convert digital signals from the [main] node assembly controller to voltage pulses for the transducer.

FIG. 15A
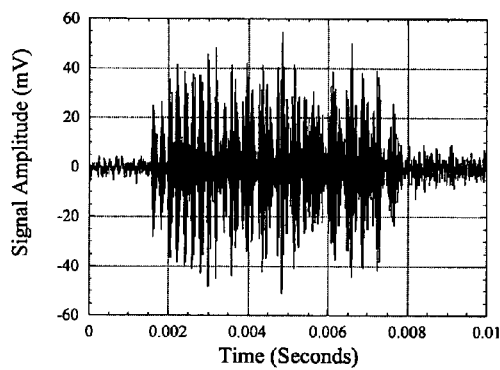
acoustic signals modulated using on-off (OOK) technique.
FIG. 15B
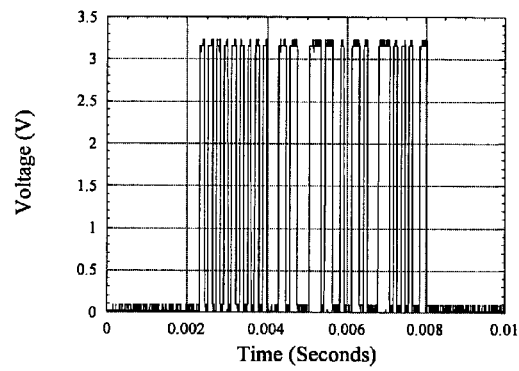
The digitized OOK moduled data package as converted
FIG. 16A
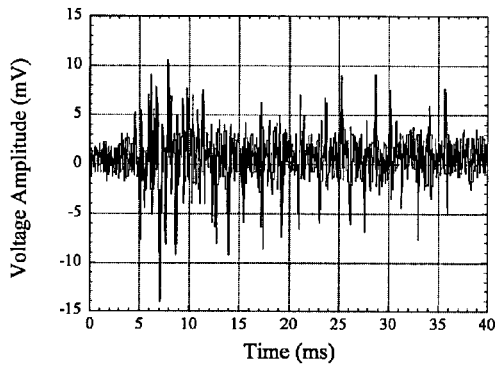
acoustic signals modulated using DPIM technique.
FIG. 16B
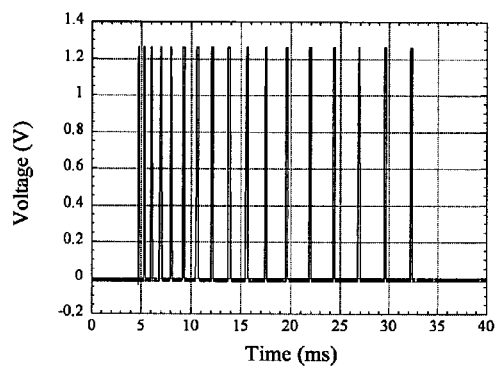
The digitized DPIM moduled data package as converted
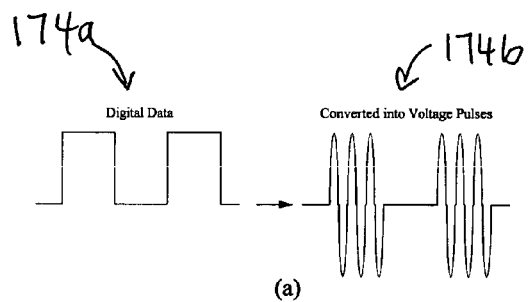
FIG. 17A
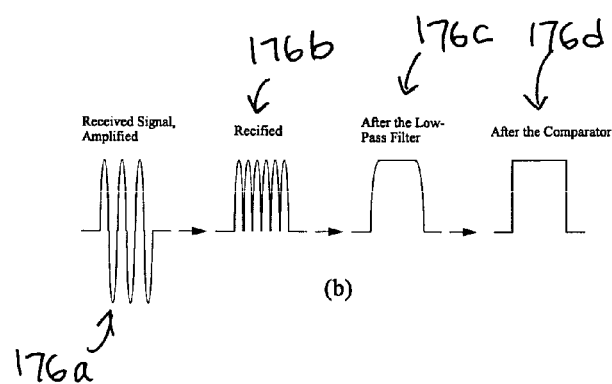
FIG. 17B

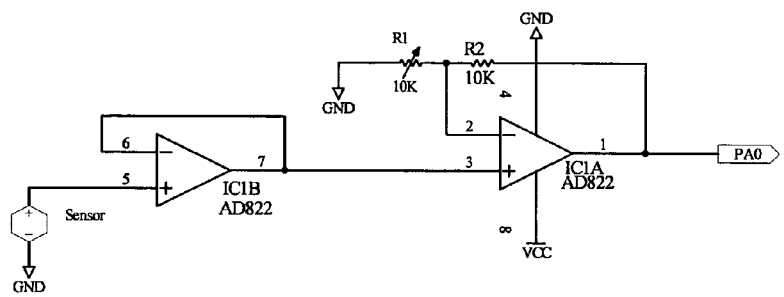
FIG. 18 sensor interface circuitry for potential-based sensors (*e.g.*, thermistors)
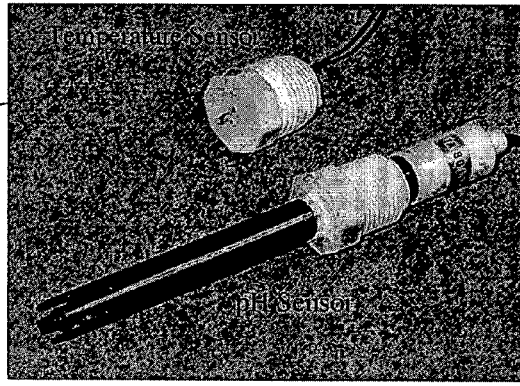
FIG. 19
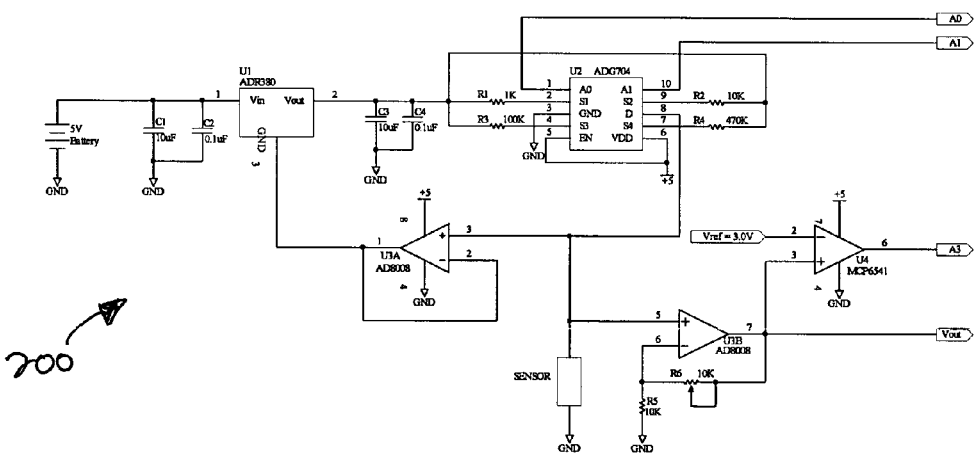
FIG. 20 sensor interface circuitry for resistive sensors.

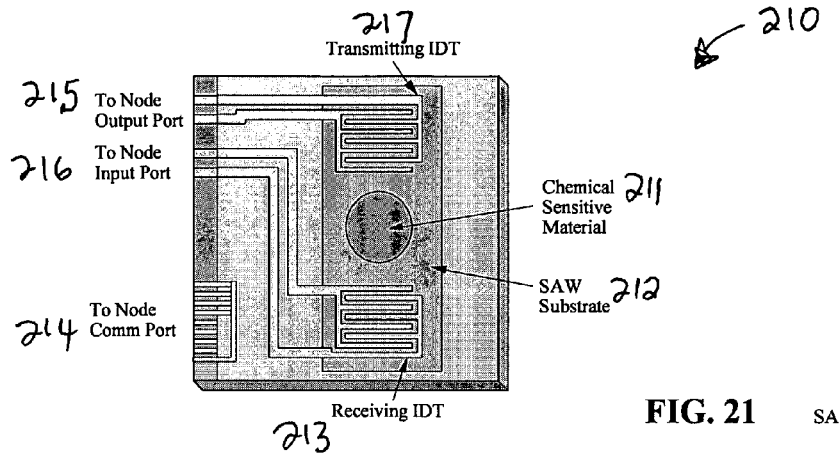
FIG. 21  SAW sensor module/element
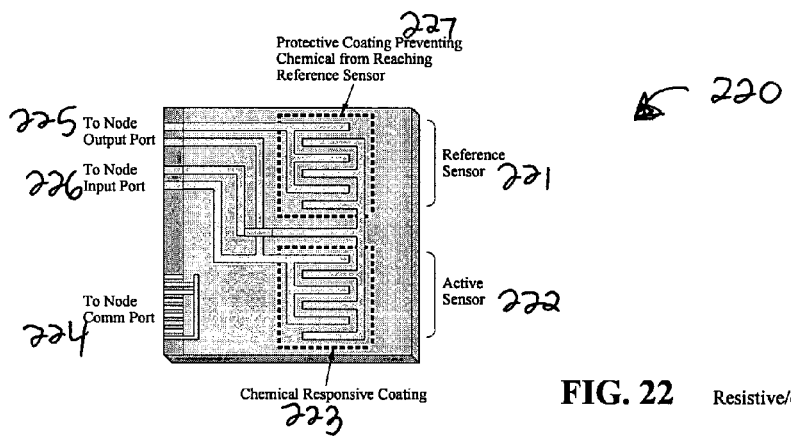
FIG. 22  Resistive/capacitive (impedance) sensor module/element
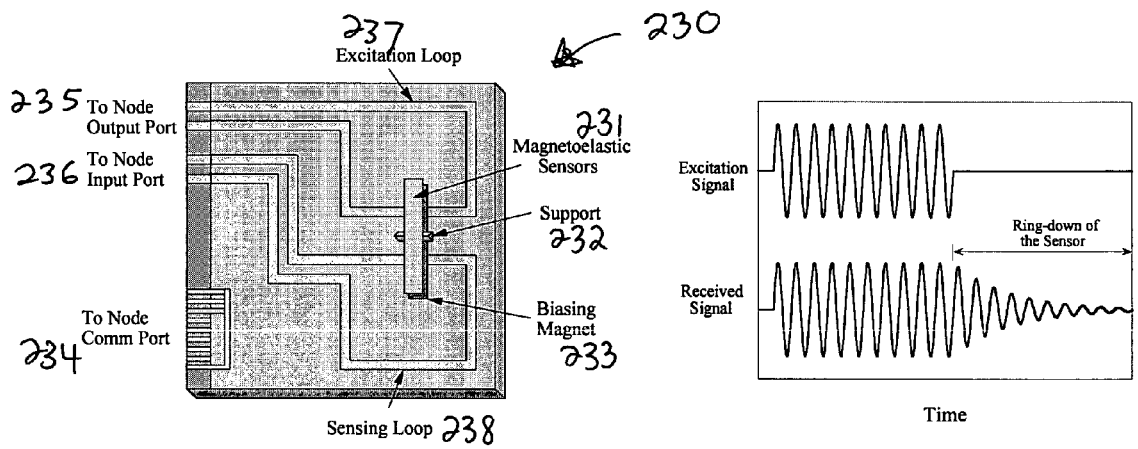
FIG. 23A  FIG. 23B

NETWORK OF SENSOR NODES ASSEMBLIES AND METHOD OF REMOTE SENSING WITHIN LIQUID ENVIRONMENTS

This application claims priority to pending U.S. provisional patent application No. 60/397,176 filed 18 Jul. 2002 on behalf of the assignee hereof.

BACKGROUND OF THE INVENTION

Field of the Invention

In general, the present invention relates to networked sensors having a multitude of intercommunicating sensor nodes dispersed throughout a medium enabling simultaneous monitoring at selected points within the medium. Sensor networks consist of an array of sensor nodes located remote from one another throughout the area of interest; the data of an individual sensor node is transmitted to a common base using other sensor nodes as relays.

More particularly, the invention is directed to a new multi-node telemetric network for use in monitoring liquids for the following applications: determining potable water sources, precision agriculture, advanced industrial process control, monitoring of aquatic biological communities (whether found in standing pools and lakes, or flowing sources such as a stream or river), monitoring of wastestream effluents, monitoring flow of liquid within pipelines, etc.; anywhere a liquid environment is identified from which information/data is desired. At the active nodes are intercommunicating sensing modules or assemblies capable of collecting 'local' physical and chemical information about a selected area of interest within a liquid environment through integration with at least one sensor element operational while immersed in the liquid. A wide variety of currently designed, and as yet to be imagined, liquid parameter collecting sensor elements having a variety of different structures may be integrated within the modules/assemblies of a network of the invention, including SAW (Surface Acoustic Wave), electrical impedance (resistive- and capacitance-type), and magnetoelastic sensors, for measurement of presence, composition, and/or concentration of selected analytes such as liquid chemical analytes and biological agents, fluid flow velocity and direction, density, viscosity, temperature, and so on. One or more of the node assemblies within the network can have additional sensor elements capable of gathering information about other parameters within the liquid undergoing analysis, or operational outside of the liquid such as one or more humidity or gas sensor element for sampling surrounding air.

The importance of developing a network sensor technology for operation in liquid environments has more-recently been highlighted in reports covering the problem of the chemical slurry of antibiotics, estrogen-type hormones, insecticides/pesticides, herbicides, PPCPs, nicotine, etc. in our nation's rivers. Water quality is of utmost importance to our future. Analysis of aqueous bodies, be it river water down stream from a sewage treatment plant, the water supply of Washington D.C., the physical and chemical composition of a local pond, lake, or well, the shoreline of the Gulf of Mexico, San Francisco Bay, or the water surrounding thermal vents on the ocean floor, is still primarily conducted in a labor-intensive manner by manual collection of physical samples that are analyzed back in a laboratory. Such sampling is expensive, time consuming, and in many instances dangerous and prone to miss short lived events such as the periodic or random release of toxins or pollutants.

Thus, and according to the invention, a very unique network and method is outlined herein which can be used for monitoring a liquid environment, such as an aqueous body, as supported by rigorous engineering analyses performed by the applicants. Applicants have discovered and hereby disclose a new network, associated technique and program code, that offers a flexible and wide reaching way to systematically collect information of interest about a liquid environment that combines a network of novel node assemblies acoustically 'interlinked' to communicate sensing information collected at each node, and further processed locally at each node (if so instructed), to transmit on for receipt by an 'uplink' node for further processing (as instructed), and then to transmit converted information from the uplink—as a collection of sensing data about the liquid environment. The unique method of the invention can be carried out based upon earlier instructions stored at the uplink node and broadcast to those nodes within range, stored locally at each respective node, or provided through message(s) broadcast from a host/base location through an uplink node and on to each respective node, or directly from the host/base to each respective node within its transmission range.

Electromagnetic signal transmission through a liquid, where there is no solid waveguide in place—such as wire or cabling—is not very effective over distances beyond a few meters unless very low frequencies are used, e.g. 100 Hz, which necessitates use of very large antennas. Since, according to the invention, information collected by sensor element(s) at each node preferably travels through the liquid environment from node-to-node as acoustic waves/energy, the range and sensing location configuration of the network, can be extended and rearranged without a corresponding increase in localized node power requirements. Acoustic wave reflection of waves having traveled through a liquid medium, such as an aqueous body, at a liquid-gas (e.g., lake-air) interface is roughly 100%. Thus, transmission of sensor information collected by the node assemblies, and acoustically transmitted within and throughout the network in a node-to-node fashion, and then on to a processor unit located outside of the liquid environment, dictates that a conversion take place, at some point, of the acoustic signals into electrical signals, electromagnetic (EM) signals, or other generally efficient transmission medium. If the unit at, for example, a host/base location where sensor information is processed or compiled into a format for downloading to removable magnetic storage media, long-term storage, or further communication to a user (e.g., government official or researcher, or anyone else that might benefit from the information) is remotely located from the last node assembly to which the sensor information had been passed, e.g., at an 'uplink' node or other 'parent' type node in acoustic transmission range with at least one other node assembly, the transmission link from that last node to the base may be by way of: EM wave/signal transmission through air or other gas; cabling-coupling assembly (fiberoptic, coaxial, or other suitable cabling protected, or otherwise insulated, from degradation by the liquid); hardwired from the node microcomputer unit to host/base microcomputer; and so on.

If the medium through which data packages/packets of sensing information are transmitted from a 'last' node to a host location is air (or other inert gas), and the last node and host are within RF communication range, yet too far for wiring or cable interconnection to be practicably implemented, transmission by RF transceiver(s) is preferably employed. Within an aqueous body, preferably communication from node-to-node is via acoustic waves to/from transducers immersed within the liquid. Since the nodes are dispersed within the aqueous body as individual units (no hardwiring connection therebetween) localized power management circuits are employed to enable the assemblies to work in a low to ultra-low power mode, thus, enabling each node to operate for extended periods on a reasonably smallish-sized electro-chemical cell (traditional-type battery) or photovoltaic cell (solar-powered battery).

General Discussion of Technological Areas, Provided by way of Reference Only:

I. Digital computers. The central processing unit (CPU) is considered the computing part of a digital or other type of computerized system. Also referred to simply as a processor, a CPU is made up of the control unit and an arithmetic logic unit (ALU)—a high-speed circuit that does calculating and comparing. Numbers are transferred from memory into the ALU for calculation, and the results are sent back into memory. Alphanumeric data is sent from memory into the ALU for comparing. The CPUs of a computer may be contained on a single chip. As is well known, the basic elements of a simple computer include a CPU, clock and main memory; whereas a complete computer system requires the addition of control units, input, output and storage devices, as well as an operating system. Once the data is in a computer's memory, the computer can process it by calculating, comparing and copying it; generally understood as follows: calculating—performing any mathematical operation on data by adding, subtracting, multiplying and dividing one set with another; comparing—analysis and evaluation of data by matching it with sets of known data that are included in a program or called in from storage; and coping—the moving of data around to create any kind of report or listing, etc., in a selected order. Instruction(s) are used to trigger computations carried out at a given node. The computation can be triggered by processing a packet carrying opcode for a given instruction for that computation. A computation operates on (i.e. takes as input and/or produces as output) one or more operands, each of which may be carried in the packet or stored, locally, at a node storage device.

II. Microelectronics—Structures and Devices. Microelectronics is that area of electronics technology associated with the fabrication of electronic systems or subsystems using extremely small (microcircuit-level) components. Since semiconductor fabrication and processing is driven by the computer-electronics industry, the demands for greater capability and faster data collection and processing of smaller-sized computerized units result in a demand for smaller-and-smaller integrated circuit (IC) microcircuits. "Chip" as may be used throughout not only the traditional use of 'chip' or 'microchip' (including any one or set of micro-miniaturized, electronic circuits, or microdevices that have been designed for use as electrical components, processors, computer memory, as well as countless special purpose uses in connection with consumer goods and industrial products), but also larger sized similarly-styled structures on the order of 1 cm to perhaps up to $10^+$ cm. The terms chip, integrated circuit (IC), and microchip are often used interchangeably within the electronics industry. By way of reference: the smaller microchips can hold from a handful to tens-of-thousands of transistors—they look like tiny chips of no more than $\frac{1}{16}$" square by $\frac{1}{30}$" thick; whereas larger-sized microchips of more than $\frac{1}{2}$-inch square, hold millions of transistors. It is generally the top one-thousandth of an inch of a chip's surface that holds the microcircuits, the substrate below provides mechanical strength and stability.

III. Data Packets and Network Messaging. A packet is any 'block' or bundle of information that has been split apart from a larger data bundle for transmission over a network. A message can be any sized set or subset of data generated for transmission over a communications message-passing medium between two physically 'remote', or separated locations (whether near or quite far apart) such as cabling, wiring, through space/air such as in RF, IR, microwave, etc., communications, through liquid by way of acoustic signals, and so on. For each data element, there may be many fields that hold the data items. Data fields are the physical storage units (typically one or more bytes in size), and data items are the individual instances of the data elements (i.e., actual data stored in the field). Packet-switching is a technique employed by and within complex telecommunications networks: Messages are split into data chunks (as packets) and the packets co-mingled and sorted over the transmission lines. A dynamic routing of telecommunications messages in the form of packets over different pathways is typically done. Often, packets representing a single message will likely not travel the same path. Each packet contains an address of origin, the address of its destination, and information about how to reunite with other related packets. There are many telecommunications protocols currently in place to support the transmission of packets (data segments), both as analog and digital information, over electrical and fiber optic lines. Packetized data representing real-time audio and video, as well as text, can be transmitted over a packet-switching telecommunications networks as well as cellular networks.

IV. Computer Memory and Computer Readable Storage. While the word 'memory' generally refers to that which is stored temporarily, storage is traditionally used to refer to a semi-permanent or permanent holding place for digital data—such as that entered by a user for holding long term. A non-exhaustive listing of known computer readable storage device technologies are categorized here for reference: (1) magetic tape technologies include QIC (minicartridges and larger data cartridges, such as those supplied by Imation Corp.), DAT 4 mm cartridges, Exabyte Corp.'s 8 mm tape cartridges, and so on; (2) magnetic disk technologies include floppy disk/diskettes, fixed hard disks (such as those in personal desktops, laptops, workstations, supercomputers, etc.), Iomega Corp.'s brand name ZIP®, HIPZIP®, JAZ®, and PEERLESS® disks, and so on; (3) optical disk technology includes magneto-optical disks, PD, CD-ROM, CD-R, CD-RW, DVD-ROM, DVD-R, DVD-RAM, WORM, OROM, holographic, solid state optical disk technology distributed by a wide variety of companies, and so on.

V. Acoustic waves and Electromagnetic waves. It is well known that electric and magnetic fields are fundamentally fields of force that originate from electric charges. Whether a force field may be termed electric, magnetic, or electromagnetic (EM) hinges on the motional state of the electric charges relative to the point at which field observations are made. Electric charges at rest relative to an observation point give rise to an electrostatic (time-independent) field there. The relative motion of the charges provides an additional force field called magnetic. That added field is magnetostatic if the charges are moving at constant velocities relative to the observation point. Accelerated motions, on the other hand, produce both time-varying electric and magnetic fields, or electromagnetic fields. Exposure of a time-varying, typically sinusoidal (termed alternating current (AC)) magnetic field will induce an associated time-varying current in a ferromagnetic sample such that it will emit EM energy.

An acoustic wave is an elastic, nonelectromagnetic wave with a frequency that may extend into the gigahertz (GHz) range. Acoustic transmission is that transfer of energy in the form of regular mechanical vibration through a medium (as a stress-wave emission). For reference, acoustics is typically categorized into divisions: infrasound, audible sound, and ultrasound, as well as three specialized studies related to each frequency range: infra-acoustics (<~20 Hz, or 20 cycles per second, below hearing threshold of a human ear), audible acoustics (from about 20 Hz-20 kHz), and ultrasonics (>~20 kHz, or 20,000 Hz). For example, an ultrasonic wave is an acoustic emission having a frequency generally above 20 kHz (just above human hearing). In addition to frequency, the study of sound is conventionally divided according to propagation medium: aeroacoustics, solid acoustics, and underwater acoustics (closely related to ocean acoustics, or oceanoacoustics). Solid acoustics and ultrasonics are interrelated: 'ultrasonics' study generally covers all three media—gas, liquid, and solid. Ultrasonic signal processing devices are useful for telecommunication, e.g., television. Aeroacoustics may be the most studied branch of acoustics: its focus is mechanical waves in gases. The speed of sound in dry air at normal temperature and atmospheric pressure is 308 m/sec. Solid acoustics is often characterized by propagation at high frequencies: A solid has 3 elastic modulii (two shear and one elongation) instead of one as in fluids (compressibility); mechanical waves in some materials may be coupled to (i.e., interact with) other waves; e.g, electromagnetic waves are coupled to acoustic waves in piezoelectrics. The study of underwater acoustics is usually lumped with oceanoacoustics: Aqueous solutions, as well as other liquids, characteristically have a low compressibility, thus a linear approach is often adequate so that, at a first glance, underwater acoustics first approximation is not much different from linear aeroacoustics. However, the real challenge is to accommodate varying conditions in the ocean, or other large bodies of water (whether still, e.g., Lake Michigan, or moving, e.g., the Mississippi River). The temperature and salt concentration in ocean (salt) water vary greatly, thus a uniform medium doesn't exist. Further, surface waves, irregular (in many cases unknown) rocks as well as non-solid deposits in the ocean or river bottom, and inclement weather over the bodies of water, are considerations in underwater acoustics.

SUMMARY OF THE INVENTION

It is a primary object of this invention is to provide a network of remote sensing node assemblies, a first and second of which each has a sensor element, as well as associated technique for transmitting information collected about a liquid environment.

The unique network, as well as associated method and computer executable program code on a computer readable storage medium, disclosed and supported herein provide the capability of sensing a select region of the liquid to collect a wide variety of types of information and data about the liquid and any surrounding environments, such as air, and transmitting from the originating node assembly to a different node within acoustic transmission range, and then transmitting further to a third node assembly where the information may be processed into a collection of data and communicated to a user, or further transmitted by way of suitable transmission medium, preferably as electromagnetic signals, to a host location for processing into a compilation of data for use.

As one will appreciate, the unique features, and/or combinations of unique features, as supported and contemplated hereby may provide advantages of information transmission, versatility in applications/functionalities, speed, efficiency, overall cost-reduction in monitoring liquid environments, and permitting reliable sensor information to be communicated to a user. Specific advantages of providing the new network, associated method and program code, will be appreciated by perusing the instant technical discussion, including the drawings, claims, and abstract, in light of drawbacks to any existing sensing network technology that might be uncovered.

There are many patentably distinguishing features of the network, method and program code of the invention. Briefly described, once again: each of at least two sensing node assemblies of the network, has at least one sensor element adapted for operation while immersed within the liquid, a source of power, and a transducer for receiving acoustic waves/signals transmitted from another of the node assemblies while immersed within the liquid. The transducer—whether comprised of multiple separate subassemblies, such as transmitter and receiver units—is preferably adapted for emitting, for transmission through the liquid, sensor information collected about the liquid by the sensor element(s). The transducer is adapted for receiving and further emitting information collected at other nodes, as a type of pass-through node for sensing information collected at other nodes.

The network also includes a third node assembly adapted for receiving and processing sensor information acoustically transmitted from other node assemblies. The third node can have its own processor unit(s) adapted for local processing, as well as an acoustic transducer adapted for receiving signals while immersed in the liquid environment, and means for transmitting sensor information to a remote host, whether that sensor information originated at the third node (if so equipped with one or more active sensor elements) or the sensing information originated or passed through other node assemblies. As contemplated hereby, means for transmitting sensor information includes a wide variety of mechanisms and/or subassemblies operational as unified functional unit, such as, for example: a radio frequency (RF) wave transceiver; a fiber-optic cable or cabling—for fiberoptic transmission at suitable wavelengths such as 850, 1300 and 1350 nm; an infrared (IR) transceiver and source; an optical transceiver, which may include a light emitting diode (LED)—an optoelectronic device that produces light for emission over a wide range wavelengths—and a device for converting electrical signals into optical signals for LED transmission; a microwave transceiver—once again, may be an all-in-one unit or separate transmitter and receiver; a connection through conductive media—which can be any suitable wiring, conductive trace material, conductive pins, etc.; and an assembly comprising a cable and a connector. While certain configurations of the means for transmitting to the remote host may be most effective for operation when not immersed in the liquid/aqueous body, such as may be the case for RF or IR communication and microwave transmission, remaining contemplated transmission mechanisms, if further employing technology to provide suitable protection from exposure to the liquid, may be used while immersed in the liquid, such as fiberoptic cable or coaxial (or other configuration) electrical cabling, hardwiring, etc., suitably insulated, encased in conduit/piping, or otherwise protected from exposure to the liquid.

The third node, if employed to further transmit to a remote host, preferably is equipped with the capability of converting sensing information received as acoustic waves/signals from other node assemblies, into electrical signals for third-node processing, and then converting into modulated EM signals for transmission on to a host computerized device, either directly or through a host node assembly having a corresponding EM transceiver and that is adapted for communicating with a computerized device equipped with an interface adapted for accessing the sensor information as a compilation of sensing data. A wide variety of types of known interface technologies may be employed to access sensor information collected and transmitted throughout a network of the invention, and aid in communicating a compilation of sensing data to a user: keyboard, keypad, mouse device, LED/light indicator pad, screen display (from simple digit or coding, to complex multimedia display), touch-sensitive screen display (whether used in connection with a pen-type subassembly, or entries are made manually, the display is projected for remote interaction/data entry, and so on), audio-transceiver coupled with voice-recognition program code, smart card magnetic strip (or other encodable media) reader, and so on.

Each of the first, second, and third node assemblies can also have acoustic-transducer circuitry for converting any acoustic waves received thereby into signals for processing locally at the node. Local node processing can include: converting any sensor information acoustically received thereby, into a collection of data about the liquid environment; converting electrical signals (whether the signals represent the collection of data, or sensing information collected at that, or another, node) into modulated signals; and further converting the modulated signals into a series of voltage pulses representing an encoding of the signals, suitable for emitting by the transducer. The converting of electrical signals into modulated signals may include employing a version of any of a number of suitable techniques such as those known and referred to in the field of communications as: On-Off Keying (OOK), Digital Pulse Interval Modulation (DPIM), Phase-shift Keying (PSK), Frequency-shift Keying (FSK), Amplitude-shift Keying (ASK), Quadrature Phase-shift Keying (QPSK), Quadrature Amplitude Modulation (QAM), and Multiple Frequency-shift Keying (MFSK). The acoustic-transducer circuitry or a local node controller having suitable processor(s) unit, may be fabricated to handle one or more of the local node processing functionalities. The acoustic-transducer circuitry may have additional functional attributes such as being capable of amplifying the series of voltage pulses prior to emission from the transducer as amplified digitized acoustic signals. The transducer may have a plurality of directional transducers, an omni-directional transducer, or other suitable configuration. While the whole of the first, second, and/or third node assemblies may be immersed within the liquid environment, only the sensor element(s) and transducer unit(s) need be immersed, at least during the time activated and operational to carry out, respectively, liquid sensing and receiving and/or transmitting functionalities. Any node assembly equipped for collecting sensing information about the liquid environment may also have sensor elements operational to sense parameters of non-liquid environments. An anchor having a releasable connection, which may also be of adjustable length, to a housing for the sensor elements may be added to any node assembly.

Node assemblies may be equipped with a great, or lesser, amount of localized node data processing capacity. By downloading more of the processing task(s)/burden to outlying and intermediary nodes, overall network data packet(s) transmission efficiency to final node location(s), may be increased. For example, those outlying node assemblies primarily designated for collecting sensing information for transmission on to another node, within acoustic range, may be equipped for processing by evaluating sensing information collected and converting or summarizing into a form for transmission, whether through one or more additional nodes, on to a parent node. As sensing information is acoustically received at a particular parent node, it may be temporarily stored for converting into a collection of data—which may be in summary format, preserving the more-important data and measurements—before converting into modulated signals for emission therefrom and on to another, 'higher-level' node location closer to a final 'base' node location. Thus, depending upon size and capacity of processing power and memory of node controller(s), as well as local source of power, a node assembly may be operational to share a greater amount of the burden to produce a final compilation or collection of data for transmission to a remote host location, for storage, for real-time use to make decision(s) about action to be taken, for further communicating with an end user, and so on. The last node through which sensing information passes, whether partially or completely immersed in the liquid during receipt of sensing information or permanently or temporarily removed from the liquid when performing its transmission functions, is preferably adapted for communicating with a computerized device equipped with an interface adapted for accessing the sensor information as a compilation of sensing data. The computerized device is preferably operational with program code for compiling and tailoring sensing information it receives into a form compatible with an intended application or use.

The third node, operational as either a host node location or an uplink node assembly, may be utilized to broadcast messages activating each node assembly within transmission range by 'waking' (if in a hibernation state) and instructing the node to collect sensing information with one or more of its sensor elements, and to further acoustically transmit a similar message in a node-to-node manner to outlying node assemblies within range, to so awaken and collect sensing information with respective sensor element(s), and so on. For example, a host may transmit a message via RF, IR, or microwave communication to an uplink node equipped with an acoustic transducer, which in turn broadcasts to each node assembly within acoustic range, and so on, until each node from which sensing information is sought has been instructed to activate. Alternatively or in addition, each node assembly may be equipped with node controller circuitry adapted for periodic, whether random, activation of the sensor element(s) of its node assembly to perform sensing. The node may be further programmed to determine if a threshold value is exceed, and if so, emit a message to those nodes within acoustic range, and on through until the message reaches the uplink or host node, of the change in conditions detected by sensing. Upon receiving the message of an exceeded threshold, the host or uplink may be programmed to perform any of a number of actions: notify and instruct all or a selection of nearby nodes to collect sensing information more often, activate other of the nodes' sensing elements to collect additional related information, provide further detailed information, in addition to any summary transmitted, and so on. For example, upon receiving such a message from a node indicating a change in conditions at or beyond an acceptable threshold level, the computerized device linked with a host node can generate an alert-type message for transmission to and through an uplink node assembly instructing outlying sensing node assemblies to decrease the interval of time between each successive activation of a sensor element to collect sensing information. Certain functionalities of the node assemblies and host location may be carried out using digital processing or analog electronic circuitry.

Any number of sensing node assemblies may be dispersed for sensing the liquid environment, provided that node groupings or clusters can be organized within node-to-node acoustic transmission range through the liquid. Nodes are preferably organized in a network branching fashion by clustering nodes around a common 'parent' node within range of other parent nodes, provides an efficient way to cover a greater region of the liquid in a manner that permits efficient transmission of data packets. For example, a hierarchy of forth, fifth, sixth, and so on, sensing node assemblies, each having at least one sensor element and a transducer for receiving acoustic waves transmitted from other nodes while immersed in the liquid environment, may be organized such that: the first and forth node assemblies are within an acoustic transmission range, respectively $r_{1-3}$ and $r_{4-3}$, of a third node assembly, a second node assembly is within an acoustic transmission range, $r_{2-1}$, of a first node assembly, and the fifth node assembly is within an acoustic transmission range, $r_{5-2}$, of the second node assembly; and so on.

In another aspect of the invention a method of transmitting information collected about a liquid environment utilizing a network comprising at least a first and second node assembly, each having a sensor element, is disclosed. Distinguishing features of the network, as identified herein, are also contemplated in connection with a method of the invention. In one characterization, core features of the method includes the steps of: (a) converting sensing information collected by the sensor elements while immersed within the liquid environment, into modulated signals; (b) acoustically emitting from each of the node assemblies, the modulated signals through the liquid environment to a third node assembly of the network; and (c) receiving the modulated signals as acoustic waves, at the third node, which can operate as an uplink or host node location, for processing thereby. Modulated signals received by the third node may be processed to convert those modulated signals into electromagnetic signals having a frequency greater than 3 kHz for transmission through air to the remote host. Once received by the host, at least partially generating a compilation of sensing data using the electromagnetic signals received. As mentioned, a wide variety of transmission means may be employed: a radio frequency (RF) wave transceiver, a fiber-optic cable, an infrared (IR) transceiver, an optical transceiver, a microwave transceiver, a connection through conductive media, and an assembly comprising a cable and a connector. The collection of the sensing information may be performed periodically, whether random, by the sensor elements. The step of converting the sensing information for acoustic emission from any one of the node assemblies may be selectively performed only if a threshold sensing value for a respective sensor element is exceeded upon sensing. Once again, in the event a multitude of node assemblies is dispersed, acoustic emission from node-to-node may be performed as follows: (a) acoustically emitting fifth modulated signals from a fifth node assembly through the second node assembly, then on through the first node assembly to a third node; (b) acoustically emitting second modulated signals through the first node assembly to the third node; (c) acoustically emitting first modulated signals to the third node; and (d) acoustically emitting fourth modulated signals from a fourth node assembly to the third node.

In another aspect of the invention, a method of transmitting information collected about a liquid environment to a remote node location utilizing a network comprising at least a first and second node assembly is characterized, having steps as follows: (a) converting sensing information collected by the sensor elements while immersed within the liquid environment, into modulated signals; (b) acoustically emitting from each of the node assemblies, the modulated signals through the liquid environment to a third node assembly of the network; and (c) receiving the modulated signals as acoustic waves, at the third node for conversion into electromagnetic signals for transmission therefrom to the remote node.

The computer executable program code on a computer readable storage medium for transmitting information collected about a liquid environment utilizing a network comprising at least a first and second node assembly, as characterized includes: (a) a first program sub-code adapted for operation at each respective of the node assemblies instructing that respective node assembly to convert sensing information collected while the sensor element is immersed within the liquid environment, into modulated signals; (b) a second program sub-code adapted for operation at each respective node assembly instructing that node to acoustically emit the modulated signals through the liquid environment to a third node assembly of the network; and (c) a third program sub-code for instructing the third node to process the modulated signals received. The program code may also include an initial program sub-code, originating at an uplink or remote host node respectively instructing the uplink or host node to transmit a broadcast message to each outlying node assembly to perform the collection of sensing information by sensor elements. The second program sub-code can comprise instructions for acoustically emitting modulated signals originating at a fifth node assembly to the second node assembly, then acoustically emitting those signals to and through the first node assembly and on to the third node.

In addition to the distinguishing features identified in connection with the network and method of the invention, additional program sub-code can be employed for: further converting the modulated signals into a series of voltage pulses prior to acoustically emitting from a respective node assembly; instructing the third node to perform processing to include converting any modulated signals acoustically received by the third node into electromagnetic signals for transmission to a remote host; instructing a remote host to at least partially generate a compilation of sensing data using electromagnetic signals received.

In another aspect of the invention, the computer executable program code as characterized includes: (a) a first program sub-code adapted for operation at each respective node assembly instructing that node assembly to convert sensing information collected while the sensor element is immersed within the liquid environment, into modulated signals; (b) a second program sub-code adapted for operation at each respective node assembly instructing that node assembly to acoustically emit the modulated signals through the liquid environment to a third node assembly of the network; and (c) a third program sub-code for instructing the third node to process the modulated signals received by converting into electromagnetic signals for transmission to the remote node.

DESCRIPTION OF THE DRAWINGS

For purposes of illustrating the innovative nature plus the flexibility of design and versatility of the preferred and alternative network configurations, and associated method and program code, all of which are supported as disclosed hereby, the invention will be better appreciated by reviewing the accompanying drawings (in which like numerals, if included, designate like parts). One can appreciate the many features that distinguish the instant invention from known sensing networks. The drawings and any attachments hereto have been included to communicate the features of the innovative network, and associated technique and code of the invention as well as the rigorous analysis performed by the applicants by way of example, only, and are in no way intended to unduly limit the disclosure hereof.

FIGS. 4 and 5 are isometric depictions of alternative node assemblies, respectively labeled 80 and 90.

FIG. 6 is a high-level block diagram of a sensing node assembly depicting sensor interface circuitry between sensor elements and a node controller as well as reference to a functional transducer unit for transmission and receipt of acoustic waves/signals.

FIG. 7 depicts components of an acoustic transducer unit suitable for use in acoustic wave transmission according to the invention.

FIG. 8 represents a data package mapping fields containing data items (individual instances/actual data of data elements) such as that which can be employed for transmission of sensing information collected and processed, as well as messages, transmitted to and among nodes of the network according to the invention.

FIG. 9 is a flow diagram depicting an embodiment detailing sequence of events of a process for activating a node assembly, including providing instructions to nodes to collect sensing information and process into a package for acoustic transmission, once modulated.

FIG. 10 is a high level diagram depicting operation flow of core events of a sensing node's microcontroller: receiving transmission from other nodes, transmitting/relaying sensing information and acknowledgement, and waiting for an acknowledgement, where ACK~acknowledgement flag, RX~receiving flag, and TX~transmission flag.

FIG. 11 is a flow diagram depicting operation flow of core events of a sensing node's co-controller, where the controller unit has been logically divided into a main and co-controller (such as is illustrated at 33 in FIG. 3).

FIG. 12 is a flow diagram depicting operation flow of core events of a computerized device in communication with a host, or central command-type, node location such as that referenced at 62 and 62' (FIGS. 1 and 3).

FIG. 13 is a schematic diagram of a transmitter circuit embodiment adapted for converting digital signals from a node controller into voltage pulses for emission through a transducer at the node.

FIG. 14 is a pictorial depicting an example of applying DPIM modulation technique on a binary code of 001010101000, thus, producing a signal comprised of voltage pulses.

FIG. 15A is a graphical representation of signal amplitude results of having modulated acoustic waves using On-Off Keying (OOK) technique; FIG. 15B is a graphical representation of the results after having converted the modulated data package of FIG. 15A using transducer interface circuitry to produce digitized OOK modulated voltage pulses for transmission from a sensing node.

FIG. 16A is a graphical representation of signal amplitude results of having modulated acoustic waves using Digital Pulse Interval Modulation (DPIM) technique; FIG. 16B is a graphical representation of the results after having converted the modulated data package of FIG. 16A using transducer interface circuitry to produce digitized DPIM modulated voltage pulses for transmission from a sensing node.

FIG. 17A graphically represents, for reference, the process of converting digital data such as that processed using a digital controller (174a) into voltage pulses (174b) for transmission from an acoustic transducer unit; FIG. 17B graphically represents the process of converting analog signals (176a) such as acoustic waves received by a node assembly of the network, into rectified, filtered signals, from which the digital state carried is extracted through a comparator, for use and processing of the final signal at the node.

FIG. 18 is a schematic diagram of an embodiment of sensor interface circuitry adapted for interfacing potential-based sensor elements such as a thermistor for measuring/sensing temperature of an environment.

FIG. 19 has isometric depictions of alternative sensor element assemblies, respectively labeled 190 (a temperature sensor/thermistor) and 192 (a pH sensor).

FIG. 20 is a schematic diagram of an embodiment of sensor interface circuitry adapted for interfacing resistive-type sensor elements (e.g., at 220 in FIG. 22) for measuring/sensing parameters of an environment.

FIG. 21 is a top plan schematic view of a Surface Acoustic Wave (SAW) type sensor element suitable for collecting information concerning liquid viscosity and density, concentration of an analyte of interest within the liquid environment.

FIG. 22 is a top plan schematic view of an impedance sensor element (or resistive-type sensor), such as that shown with an interdigital capacitor coated with a layer selected for its response to exposure to an analyte of interest within the liquid environment.

FIG. 23A is a top plan schematic view of a magnetoelastic-type sensor element for use to monitor an analyte of interest within the liquid environment; magnetoelastic sensor elements are suitable for collecting a wide range of information about analytes as well as a variety of parameters of liquid and gas environments. FIG. 23B graphically depicts a pulse-modulated sinusoidal excitation signal and, beneath it, the sensor's response to having been exposed to the excitation signal—both of which are characteristic of operational features of the sensor in FIG. 23A.

DETAILED DESCRIPTION OF EMBODIMENTS DEPICTED IN DRAWINGS

Figure 1:
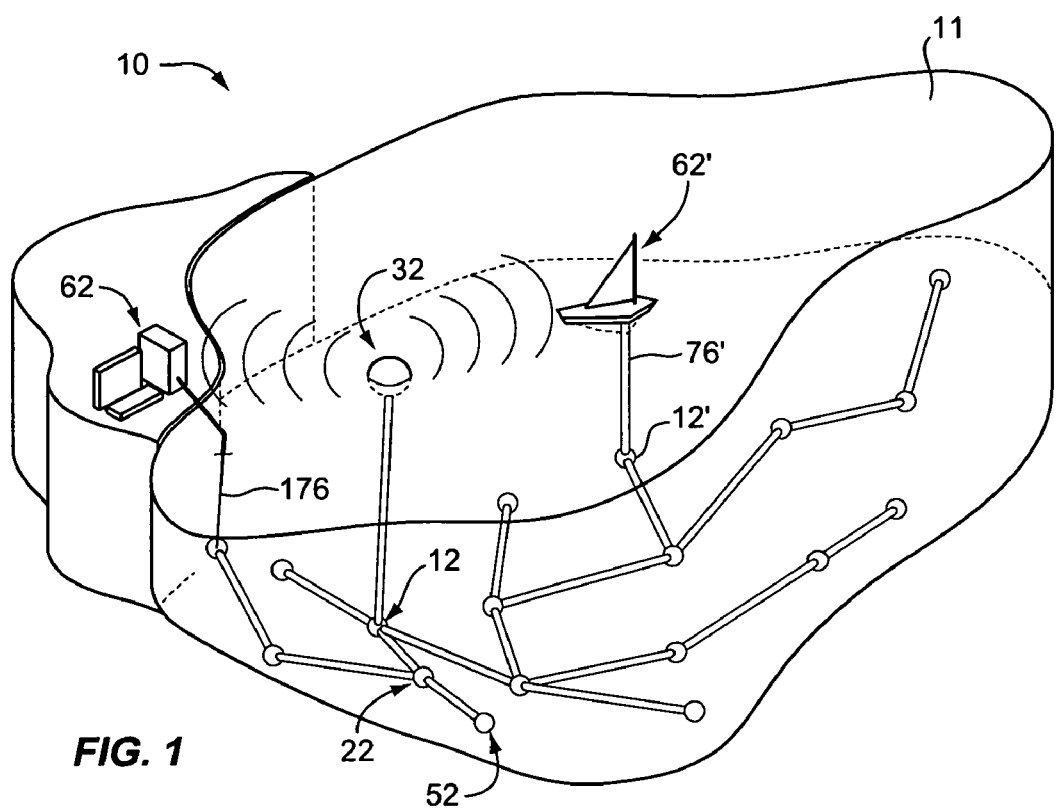
FIG. 1 diagrammatically depicts an embodiment of a network 10 for sensing a liquid environment according to the invention, having an uplink type node assembly 32 capable of transmitting outside the liquid boundary to remote locations at 62 and 62'.

In connection with discussing the several figures, occasional back-and-forth reference will be made to the flow diagram of FIG. 24, which details core and further distinguishing features of a technique of the invention at 240. FIG. 1 diagrammatically depicts an embodiment of a network 10, including preferred core and further distinguishing features, for sensing a liquid environment according to the invention. An uplink type node assembly 32 is partially immersed within liquid environment 11, and as depicted is capable of transmitting outside the liquid boundary to, and is within range of, remote locations 62 and 62'. In the event the liquid environment 11, as shown, is an aqueous body such as a lake, reservoir, river, pond, including guarding water passages such as a busy city or military port, the aquatic network may have a shore location 62 and/or a floating or submerged vessel 62' as host location. As labeled, the sensor network consists of an array of nodes 12, 12', 22, 52 and others not labeled, submerged at different locations in the body 11. Data of an individual sensor node is transmitted to a common base or host node location 62, 62' using other nodes as relays; neighboring nodes within range are shown with interconnections as solid tubular-type links for purposes of reference only, as no physical interconnection between nodes is anticipated. Acoustic wave reflection at the water/air interface will be overcome via an uplink node 32, which is shown for example, as a partially submerged buoy equipped with acoustic to electromagnetic signal conversion capability. Several alternatives to this configuration are contemplated. Host node assembly 62 (see also, FIG. 3) can be placed in the liquid body 11 equipped with acoustic transceiver capability to acoustically intercommunicate with nodes that are immersed, and also connected via cable or wiring to a host computer (64 in FIGS. 2 and 3). Host node assembly may be physically located outside of the aqueous body 11, as shown at 62, 62' with cable or hardwired connection, respectively at 176, 76', between the host and an immersed node. Host node assembly may be located inside a submerged vessel in communication with a computerized device (e.g., 64) via cabling and hardwired/cable-connected through appropriate hatch-opening, to a sensing node on the exterior of the vessel.

The network 10, 20, 30 (FIGS. 1-3) of nodes has both a network intercommunication and a transmission operational mode. The communication mode is used for (1) activating the sensor nodes, whether remotely from or through an uplink 32 or in a self-activation manner whereby the nodes are programmed to periodically awaken from a hibernation state to collect sensing information, and (2) establishing a path for the sensor nodes to transmit data toward a 'home-base' (e.g., uplink 32, shore 62, floating 62'), through branched clusters with parent nodes. During communication mode using a host/base, the base station broadcasts an activation signal through an uplink 32 and on to branches of neighboring nodes. Upon receiving the activation signal, each respective node remembers the base station as a host location and, in the event clusters of neighboring nodes with a 'parent' node are formed, the parent nodes are remembered, until all levels of branched nodes, including the outermost outlying nodes, have been reached. After which, the network of nodes, in turn, send out activation signals through their parents and back to the base station. This process is repeated until all nodes in the network know the identities of their parents. When multiple activation signals are detected, the sensor nodes are preferably equipped to determine which activation signal is coming from a parent node.

Figure 2:
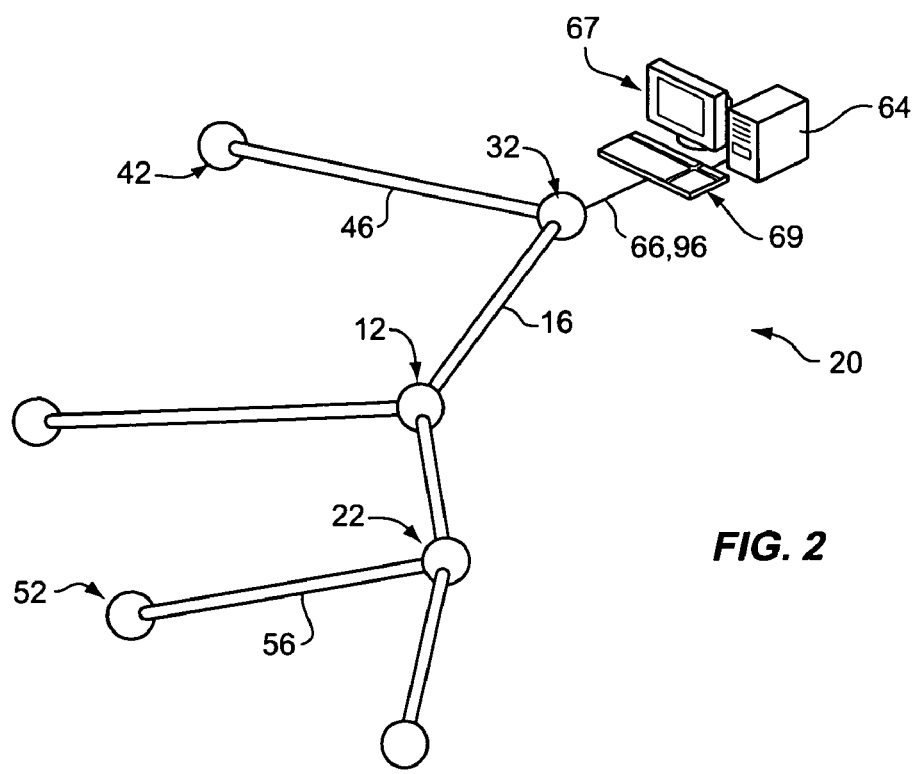
FIG. 2 is a pictorial representing one embodiment depicting a network 20 organized in a branched fashion according to the invention.

The FIG. 2 embodiment illustrates network 20 organized in a branched fashion with either an uplink node, or sensing node assembly operational as a parent of a cluster of nodes, at 32. As viewed in connection with FIG. 3, using common reference numbers, computerized device 64 with storage 67 and interface 69 is interconnected to node 32 through EM signal communication medium 66 or 96. Sensing node assemblies 42 and 12 are respectively in acoustic wave intercommunication at 46 and 16. Node assembly 12, as a parent node, is in acoustic intercommunication 26 to node 22 as well as an unlabeled furthest-outlying node. Node assembly 22, also as a parent node, is in acoustic intercommunication 56 with a furthest outlying node 52 and another unlabeled node. FIG. 2 will be reviewed in connection with FIGS. 9-12 and details concerning sample network protocol for organizing node assemblies within the liquid environment for effective ongoing intercommunication.

Figure 3:
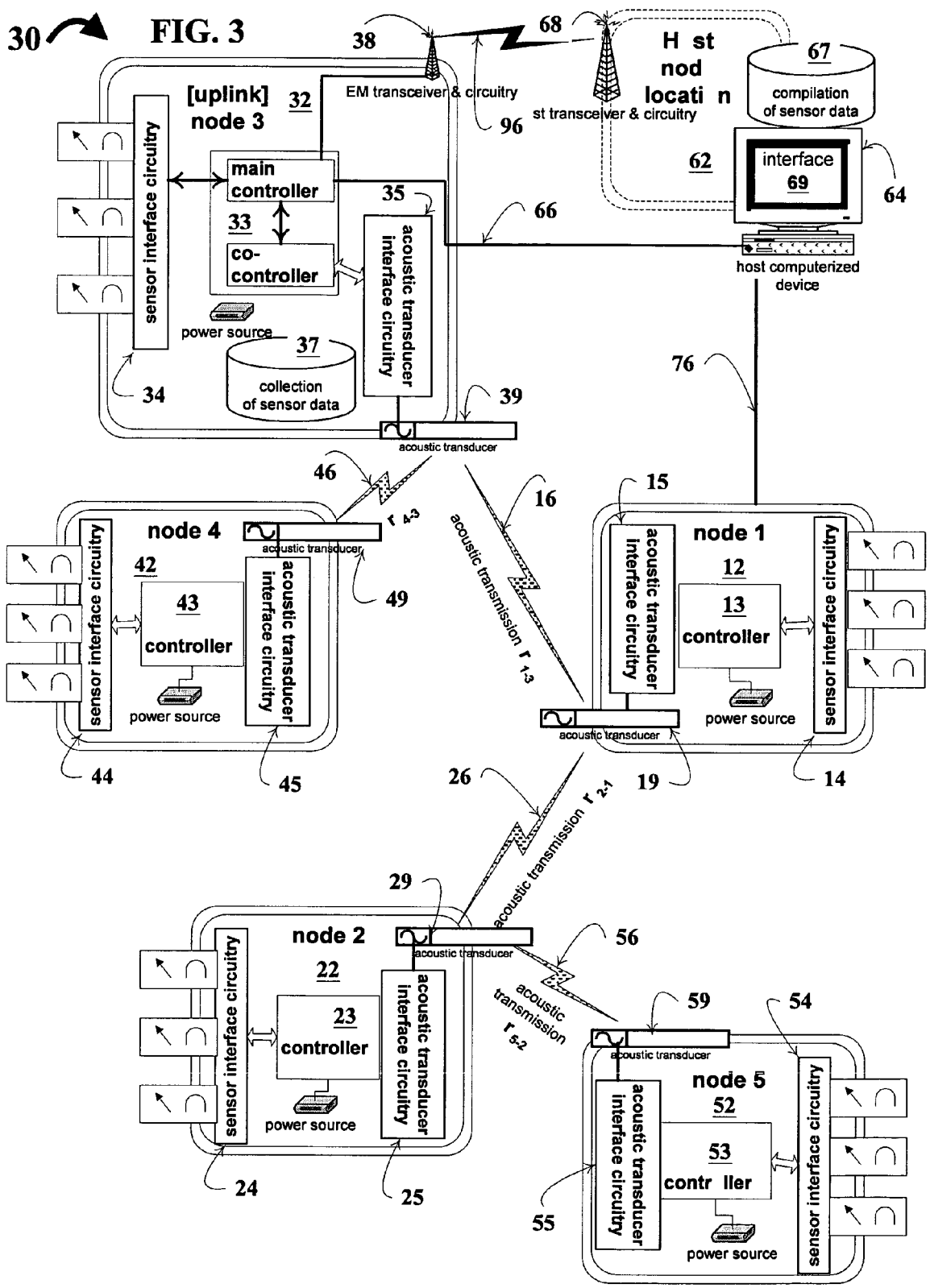
FIG. 3 diagrammatically represents core as well as further distinguishing features of a network 30 of the invention having a couple of levels of branched clusters of nodes, by way of example.

FIG. 3 diagrammatically represents core as well as further distinguishing features of a network 30 of the invention having a couple of levels of branched clusters of nodes, by way of example. Components of the host node location 62 are shown with alternative means of intercommunication 96, 66, 76 with the network 30 of node assemblies 32, 42, 12, 22, and 52. A host transceiver/coupling 68 interconnected with a host node assembly provides a means by which EM signals transmitted from a transceiver 38 associated with node assembly 32, may be received with or without hard-wire/cable connection. Either internal cabling/hardwiring or other intercommunication may be employed to communicate with a host computerized device 64 and its user-communication or data-entry interface 69. As shown, a direct interconnection medium 66, 76 may be employed to connect respective node assemblies 32, 12 with computerized device 64. Alternatives for the EM signal intercommunication link labeled 96, as well as those at 66 and 76, include any suitable for handling transmission of information/data converted to EM signals at node 32 such as RF, IR, microwave transmission, fiberoptic or electrically conductive cabling/wiring, and so on. The transmission medium is preferably selected to minimize exposure to a liquid or other corrosive environment; however, if exposure is expected, suitable insulation, conduit, or other protection from degradation of component cabling/wiring, coupling(s), transceiver housing(s), etc., will be used.

Node 32, which may operate as an uplink node, has by way of example only, its controller 33 logically subdivided into a main controller and co-controller subunits. The controllers 13, 43, 23, 53 of each of the sensing node assemblies 12, 42, 22, 52 can likewise be functionally subdivided, or not. Sensor interface circuitry 34, 14, 44, 24, 54 of each node provides interface functionality between each of the various sensing elements (not labeled) respectively incorporated with node assemblies 32, 12, 42, 22, 52. While the sensor elements selected for incorporation with each respective node assembly may be the same, they need not be. For example, certain nodes may be located for sensing one set of parameters and conditions, where other nodes are tailored to check concentration and presence of one or more analytes of interest, whether underwater or above the aqueous body. Acoustic transducer interface circuitry 35, 15, 45, 25, 55 of each node provides interface functionality between each of the various acoustic transducer units, respectively, 39, 19, 49, 29, 59 and the local node controllers 33, 13, 43, 23, 53. Acoustic transmission between and among nodes within range of one another is labeled, for reference, as follows 16 ($r_{1-3}$), 46 ($r_{4-3}$), 26 ($r_{2-1}$), and 56 ($r_{5-2}$); as a schematic, one can appreciate that FIG. 3 is not to scale. As organized, here, sensing information originating from, and messages traveling to/from, node 5 (52) go through node 2 (22), then node 1 (12), before reaching uplink node 3 (32). Likewise, sensing information originating from, and messages traveling to/from, node 2 (22) go through node node 1 (12), before reaching uplink node 3 (32).

A 'local' power source (labeled as such) has been incorporated with each node assembly 32, 12, 42, 22, 52. The many suitable sources of power contemplated include any that provides operation over the length of time nodes will be dispersed within the liquid, as tailored to power requirements for on-board circuitry and local data processing and transmission capabilities. As can be appreciated in connection with the flow diagram of FIG. 9 as well as FIGS. 18-23A/B, integration of different sensor element families via sensor interface circuitry is multifaceted challenge, as different types of interrogation signals will be needed to operate different families of sensor elements, which will in turn produce different output forms. For example, a capacitive sensor will use a steady state AC electrical interrogation signal, while magnetoelastic sensors may require a magnetic pulse. Preferably each sensor node will be equipped with signal processing circuitry to extract needed signal information from the sensors, such as amplitude, frequency, and phase delay. In an effort to maintain design flexibility, a modular plug-in format can be used to accommodate incorporating replacement elements for upgrade or repair. A multiplexer may be employed to switch between the sensor element modules so the node can interrogate one module at a time.

The program code used at the sensor node may contain a core program controlling communication between sensor nodes, and a number of independent subroutines to control the functions within the node assembly. Long term monitoring may be achieved by maintaining node assemblies in a low-power standby or hibernation/'sleep' mode, until a signal is received to activate the node. As can be appreciated in connection with FIG. 24, the node activation signal may come from a host node location through an uplink (step 242), or may be generated 'locally' at the node (248) on a timer set for periodically waking a hibernating node assembly, to collect information about the environment(s). The sensing information may be stored for later processing, use or transmission; or, if a threshold value is exceeded as programmed, the node may take further more-immediate action such as converting the information into modulated signals (step 250) and acoustically transmitting (step 252) through the network to notify the host node location to broadcast an alert message (step 242) to the other nodes to sense more-frequently or immediately, and so on. In this fashion the sensor nodes consume little power, for example less than 30 μW, allowing them to be powered by quarter-sized lithium coin cells (2.5 cm diameter, 1 cm thick) for several years. Throughout monitoring of the environment(s) (step 262) activation signals may be sent periodically (242) or from within (248) to awaken the sensor network, and re-establish links between nodes that may have drifted or been moved (e.g., step 245).

FIGS. 4 and 5 are isometric depictions of alternative node assemblies, respectively labeled 80 and 90. Depending upon the application and selected local functionalities, node assembly housings may be smaller than a baseball or as large as a 13-gallon bucket. Once again, each sensor node may contain a variety of different types of chemical, biological, and physical sensors to collect a variety of information about the liquid and surrounding environment(s). Sensing node assembly 80 of FIG. 4 is shown with several sensor elements 82 supported by a platform encased in mesh capsule like cover 83 allowing the liquid to flow over sensor elements, to collect information about the liquid environment, while preventing debris from harming sensor components. Hydrophone 85 for emitting acoustic signals is engaged atop battery and circuitry encasement 84 is releasably engaged to an anchor unit 88 by way of actuator instructed by node control. The anchor unit operates to maintain the housing 84 and sensor elements 82 at a depth (height above bottom) for collecting sensing information. Alternatively, unit 88 may be a water/liquid ballast unit, the contents of which can be replaced with water or other gas, lighter than the liquid, to permit the node 80 to float to the top of the liquid surface for maintenance or removal. Sensing node assembly 90 of FIG. 5 is shown with several sensor elements 92*b* in sensor sockets 92*a* supported by an enclosure/capsule 93 allowing the liquid to flow over sensor elements, to collect information about the liquid environment. Acoustic transducer unit 95 has an acoustic absorber disk atop piezoelectric (PZT) ceramic tube transducer. A cable connecting enclosure 93 and anchor 98 is provided 97*a* for use to retrieve anchor unit 98 once enclosure unit 93 is released to the surface for maintenance or removal from liquid the environment. A second cable is shown 97*b*, for which a coiling is encased at 99 and secured to anchor 98, which may be used to adjust the height of sensor elements 92*b* from the bottom of the liquid environment. Upon receiving instructions from the node controller, a latch (such as a magnetic latch mechanism) may be disengaged thus allowing the enclosure 93 to rise to the top surface of the liquid.

FIG. 6 is a high-level block diagram of a sensing node assembly 112 depicting sensor interface circuitry between sensor elements and a node controller as well as reference to a functional transducer unit for transmission and receipt of acoustic waves/signals. Three sensor elements are interfaced to the node controller 113 via sensor interface circuitry 114. Wake-up circuitry in communication with transducer 119 provides functionality as described to activate a node in hibernation mode, or to periodically awaken the node according to random or equally spaced time intervals, to engage one or more of the sensor elements to collect information (see also diagrams labeled FIGS. 9, 12, and 24). As mentioned, the transducer unit 119 may be composed of one or more components including transceiver, an omni-directional or several directional transmitters, receiver, an encasement(s), and associated acoustic wave/signal to electrical signal conversion circuitry.

FIG. 7 depicts components of an acoustic transducer unit 129 suitable for use in acoustic wave transmission and receipt according to the invention. The transducer shown is a piezoelectric (PZT) ceramic tube 129*a*. As further explained below, two matching layers made of aluminum 129*b* and poly(vinyl chloride), PVC, 129*a* are used to match the acoustic impedance of the PZT ceramic to water in the radial direction. The damping material (disk 129*d*) may be made of rubberized magnet and is placed on top of the transducer to reduce the acoustic transmission in the vertical direction (hence reduces the reflection from the water-air boundary).

Transducer Design Considerations. The transducer, as an integral part of each underwater node, is the device that converts electronic signals used by node circuitry into acoustic waves and emits them into the liquid environment, and also receives acoustic waves and converts them into electronic signals, i.e., it is the physical device performing the acoustic-electronic conversions. Preferably the transducer(s) is fabricated using a piezoelectric material component. The transducer assembly preferably has omni-directional directivity capability in at least the horizontal plane, in order to project and receive sound waves to/from any azimuthal direction. This may be accomplished by the use of either a single omni-directional transducer or an array of directional transducers geometrically arranged to obtain omni-directional capability. The tasks of sound generation and sound reception can be performed by either a single transducer or by separate transducers/arrays, each optimized for operation either as a projector or as a hydrophone. Other feature considerations of the transducer assembly include: (a) achieve maximum acoustic power/sensitivity while minimizing power draw; (b) the geometry should be such that the sound power incident on the surface of the water body is minimum so as to minimize reflected wave intensity and corruption of signals of interest; (c) assembly is packaged by acoustic impedance matching layer(s) to maximize efficiency; (d) geometric dimensions and weight are compatible for incorporation within the node assembly structure(s); (e) physically mountable on a node assembly to carry out its function(s) such that the physical mounting selected tends towards minimizing mechanical clamping (to increase efficiency).

TRANSDUCER EXAMPLE 1

Quarter Wave Matched Layer Omni Directional Reversible PZT Piezoelectric Cylindrical Transducer. The cylindrical omni-directional transducer (toroidal beam pattern) is made of Lead Zirconate Titanate (PZT), with an outer diameter of 15 mm, inner diameter of 1-3 mm, and length of 17 mm. The inner and outer walls of the tube are coated with silver electrodes. An aluminum tube with an inner diameter of 15 mm and outer diameter of 42 mm is adhered to the outer wall with conductive epoxy to form the first acoustic matching layer; it also acts as the ground plane for the transducer. A poly(vinyl chloride) (PVC) tube with an inner diameter of 42 mm and outer diameter of 52 mm is glued to the aluminum as the second matching layer. These two matching layers increase the acoustic transmission in the radial direction by reducing reflection due to the acoustic impedance mismatch between PZT and water. An acoustic absorbing disc (diameter of 152 mm, thickness of 8 mm) made of rubber is glued on top of the transducer to reduce the acoustic emission to the water surface, which minimizes the reflection from the water-air boundary. A double-sided printed circuit board (PCB) disc is placed at the bottom of the transducer. A ring (4 mm in diameter, 1 mm in thickness) is etched from the PCB, separating the center portion, which is used as the signal plane, and the outer portion, which is the ground plane. The signal plane is connected to the inner wall of the PZT with a wire, and the ground plane is connected to the outer wall of the PZT by gluing to the aluminum with conductive epoxy. An SMA connector is soldered on the PCB so its signal line is connected to the center portion of the PCB and its ground to the outer portion of the PCB. The packaged transducer is connected to the sensor node circuit via SMA cabling.

Transducer Material: As mentioned, the transducer material preferably displays piezoelectric properties. Though there are hundreds of materials which display piezoelectricity, it is important that this property is present in sufficient strength for application, here. These include Lead Zirconate Titanate (many different relative compositions of Lead Zirconate and Lead Titanate, pure and doped, are possible), Barium Titanate (pure and doped), Strontium Titanate (pure and doped), Barium Strontium Titanate (again, many different relative concentrations, pure and doped, are possible), Poly(Vinylidene fluoride) and its co-polymers, Quartz, the relaxor ferroelectric materials Lead Magnesium Niobate (PMN) and Lead Magnesium Niobate-Lead Titanate (PMN-PT), etc.

TRANSDUCER EXAMPLE 2

Omni Directional Reversible PZT Piezoelecthic Cylindrical Transducer with End Caps and Rubber Impedance Matching Layer. EDO Electro-Ceramic Products, Salt Lake City, Utah distributes transducers with these characteristics. The dimensions are 0.87" OD×2.37" length. The ceramic cylinder is 'closed' (air backed) by means of two metal end-caps. This assembly is packaged in a rubber impedance matching layer (polyurethane was used, though neoprene or the so called 'rho-c' rubber will also work). Each transducer has a 24" long cable.

FIG. 8 represents a data package 120 mapping fields containing data items (individual instances/actual data of data elements) such as can be employed for transmission of sensing information collected and processed, as well as messages, transmitted to and among nodes of the network according to the invention. Package 120 has header information 126, two fields labeled "Destination" and "Origin" for tracking the package travel route, as well as data fields 128 for information collected by the various sensor elements.

FIG. 9 is a flow diagram depicting an embodiment detailing sequence of events of a process 130 for activating a node assembly, providing instructions to collect sensing information and process into a package for acoustic transmission, once modulated. As depicted in the commentary provided within the blocks of process 130, the node controller program code may consist of a core program that controls inter-node communications within the liquid environment, with subroutines to control the various sensor platforms. The uplink node (e.g., 32 in FIGS. 1 and 2) will also have sub-code program modules to carry out conversion into EM transmission to the host/base (62, 62' in FIGS. 1 and 2). After receiving an activation message from a neighboring node, that node will be stored as a parent. After all sensor modules within a node are interrogated the program code may combine the response of all sensor elements into one data package, add the identity of its parent as the destination and its own identity as the origin, and then transmit the data package. When a package from another node is received at that node assembly, the controller will pause, or interrupt, current operation and compare the destination identity of the package to its own identity. If the node identity does not match it will resume its previous operation, as it will be understood that the destination is elsewhere. If the identity matches, the program will replace the destination with its parent, send the package to its parent, then resume any internal operation(s) it had been performing.

FIG. 10 is a high level diagram depicting operation flow 140 of core events of a sensing node microcontroller embodiment; core elements, as specified on the flow diagram, include receiving transmission from other nodes, transmitting/relaying sensing information and acknowledgement, and waiting for an acknowledgement, where ACK stands for acknowledgement flag, RX stands for receiving flag, and TX stand for transmission flag.

MICROCONTROLLER EXAMPLE 3

The following is provided by way of example only in reference to FIG. 10: When the RF or acoustic transceiver receives a signal, it setups an interrupt flag (RX flag) to instruct the microcontroller to download the data from the transceiver. The microcontroller then engages the receiving handler, which can process the data and determine if the signal is a broadcast, acknowledgement, or sensor data. If the received signal is the sensor data from other nodes, the microcontroller program will relay the data to its parent node by triggering the transmission flag (TX flag) and data relay flag. If the received signal is a broadcast signal, it will trigger the TX flag and also an acknowledgement flag. After setting the flags, the program returns to the main loop. An internal timer is also running while the microcontroller performing all these processes. When the timer reaches a prefixed time interval, it also triggers the TX and data relay flags to upload its own sensor data.

When the TX flag is triggered, the microcontroller engages the transmission handler. If the relay flag is also activated along with the TX flag, the handler will encode the sensor data into a packet, forward it to the transceiver, and then return to the main loop. On the other hand, if the acknowledgement flag is triggered with the TX flag, the program will launch the wait acknowledgement handler. Within the wait acknowledgement handler, the program actively checks for the RX flag. The program waits until it receives an acknowledgement signal or time out.

CO-CONTROLLER MODEL EXAMPLE 4

FIG. 11 is a flow diagram depicting operation flow 150 of core events of a sensing node's co-controller, where the controller unit has been logically divided into a main and co-controller (such as is illustrated at 33 in FIG. 3). The following is provided by way of example only in reference to FIG. 11: After the sensor node is powered on, the co-controller actively waits for an incoming signal, be it from the main controller or transducer. If the co-controller receives a signal from the main controller, it will synchronize its reading speed with the baud rate of the data. Upon successful capturing of the data, the co-controller performs a checksum operation to determine if the data is corrupted. If the captured data passes the checksum test, the co-controller encodes the data to a series of voltage bursts—a series of 10 voltage bursts (the carrier frequency is 110 kHz) represents a digital state of '1', and zero voltage for the duration of 10 voltage bursts represents a '0'. When a transmission from a neighboring node within transmission range is captured by a transducer of a node assembly, it is sent to the transducer interface circuit (e.g., FIG. 3, 15, 25, 35, 45, 55) for converting into digital data (see FIG. 17B). The converted data is sent to the co-controller for processing. Similarly, the co-controller may be engaged to determine the legitimacy of the data, decodes the data to the format required by the main controller, and then forwards it to the main controller.

FIG. 12 is a flow diagram depicting operation flow 160 of core events of a computerized device in communication with a host, or central command-type, node location such as that referenced at 62 and 62' (FIGS. 1 and 3). One function of the host computer 64 is to instruct the host node 62 or 62' to send out broadcast signals and download the sensor data from the host node. After obtaining the sensor data, the host computer will process and present it to the users. The operation of the host node assembly (e.g., at 62, FIG. 3) will have additional features than sensing nodes (e.g., at 12, 22, 32, 42, 53, FIG. 3) since it has to interface with the host computer (PC) at 64.

HOST CONTROLLER MODEL EXAMPLE 5

The following is provided by way of example only in reference to FIG. 12: In addition to checking for the receiving, acknowledgement, and transmitting flags, the host node also checks for a PC interrupt flag. When the PC interrupt flag is triggered, the host node may downloads the data from host PC 64 via RS232 interface, which has the format of:

| Command | Parameter A | Parameter B |
| --- | --- | --- |
| XX | XX | XX |

The Command contains the operation instruction for the host node: 01 means sending broadcast signal, 02 means uploading all sensor data to host PC 64, 03 means changing the time interval between each broadcast, and 04 means changing the time interval between sensor data collection. The Parameter A and Parameter B are used for Command 03 and 04 for entering the values of the time interval. In specific, Parameter A sets the value and Parameter B sets the unit (01=seconds, 02=minutes, 03=hours, 04=days, 05=weeks). For example, an output from the host PC with the data of 04,30,02 changes the time interval between the sensor data collection to 30 minutes.

FIG. 13 is a schematic diagram of a transmitter circuit embodiment 170 adapted for converting digital signals from a node controller into voltage pulses for emission through a transducer at the node. Note throughout that, while the figures depict components of digital processing, by way of example, the network, method, and program code of the invention is suitably carried out using analog electrical component equivalents, as contemplated hereby.

Transducer interface circuitry 170 (see, also, FIG. 3 at 15, 25, 35, 45, 55) may consist of two functional parts: transmitter circuitry and receiver circuitry. The transmitter circuit may include an amplifier for amplifying the output voltage pulses from the co-controller. The co-controller generates different kinds of signals depending upon the modulation technique selected. Although different signal modulation techniques may be used according to the invention, here, focus is on a type of on-off modulation (referenced herein, as OOK) and Digital Pulse Interval Modulation (DPIM). During OOK modulation, the controller generates a series of positive voltage pulses to represent a '1' and zero voltage for the same duration to represent a '0'. The number of pulses can be 1 to a few hundreds depending upon the transducer design and operating conditions. Using DPIM, which conveys digital information by the time-interval between two consecutive '1' states, the microcontroller will first sends a series of pulses for a '1' state, and then waits for the appropriate duration before sending the second '1'.

FIG. 14 is a pictorial depicting an example of applying DPIM modulation technique on a binary code of 001010101000, thus, producing a signal comprised of voltage pulses.

FIG. 15A is a graphical representation of signal amplitude results of having modulated acoustic waves using On-Off Keying (OOK) technique. FIG. 15B is a graphical representation of the results after having converted the modulated data package of FIG. 15A using transducer interface circuitry to produce digitized OOK modulated voltage pulses for transmission from a sensing node. FIG. 16A is a graphical representation of signal amplitude results of having modulated acoustic waves using Digital Pulse Interval Modulation (DPIM) technique. FIG. 16B is a graphical representation of the results after having converted the modulated data package of FIG. 16A using transducer interface circuitry to produce digitized DPIM modulated voltage pulses for transmission from a sensing node. Regardless of the modulation technique selected, it is preferable to use an output signal of the node assembly's (micro)controller that is positively biased. Signals received by a transducer (FIG. 3 at 19, 29, 39, 49, 59) from a controller unit are preferably first amplified and rectified, and the voltage pulses are preferably converted to digital data with a low pass filter and a comparator. The converted data packages are shown in FIGS. 15B and 16B. Since signals received by a transducer (for reference see FIG. 3 at 19, 29, 39, 49, 59) will likely contain noise, the signals received are filtered and amplified before being sent to the controller units (FIG. 3 at 13, 23, 33, 43, 53), whether that controller unit is logically partitioned into a main and co-controllers, such as at 33, FIG. 3 (see also, discussion regarding processes depicted in FIGS. 10 and 11).

For reference purposes, FIG. 17A graphically represents an example of the process to convert digital data such as that processed using a digital controller (174*a*) into voltage pulses (174*b*) for transmission from an acoustic transducer unit; FIG. 17B graphically represents the process of converting analog signals (176*a*) such as acoustic waves received by a node assembly of the network, into rectified (176*b*), filtered signals (176*c*), from which the digital state carried is extracted through a comparator (176*d*), for use and processing of the electric signal at the node.

DIGITAL SIGNAL MODULATION
TECHNIQUES EXAMPLE 6

Due to the impediments of attempting electromagnetic communication in a liquid, such as water, the network of the invention utilizes acoustic waves. Operating frequency selection takes into account two competing attributes: lower frequencies propagate with less loss, while higher frequencies have greater data transmission rates. Frequency range includes 1 kHz to 1 MHz, as a trade off between propagation and data transfer rates, one might select an acoustic carrier wave frequency of 50 kHz. At 50 kHz, an acoustic wave can travel at least ~500 times further than an EM wave through water. The communication frequency, like many other system design parameters, is selected for optimal performance given the operating conditions of a specific application in the later stage of this work. Data collected by sensor elements is preferably digitized and translated into a binary code. DPIM may be used to conserve power at the node. The time interval between two successive pulses may be set equal to the interval between one pulse and eight pulses depending upon the data (one pulse duration represents a digital state of 0, 2 pulses represent 1, 3 pulses represent 2, and so on). For example, return to FIG. 14: modulation of a binary code 001010101000 using DPIM. DPIM converts the binary data to a base-8 number (combines every three bits together), so the binary code becomes 1250 (base-8).

There is a large impedance mismatch at water/air and water/ground boundaries, hence acoustic waves are strongly reflected from these layers. Therefore a receiver may receive both the originally transmitted wave, as well as a reflected wave. The reception of both original and reflected waves results in unwanted modulation of the detected signal can cause data error(s). Fortunately, the reflected waves take longer to reach the receiver than the direct wave due to its greater travel path. Therefore, if the data is compressed into a series of short bursts the receiver can finish its reception before arrival of the reflected wave. Like frequency, the burst time is another design variable dependent upon the application, e.g. lake or river, ocean or small waste stream. For example, consider nodes at least 15 m under water with a separation distance of 40 m. With the speed of sound ≈1500 m/s in water, the acoustic wave will take 27 ms to travel directly from the transmitter to receiver, and the water/air reflected waves will begin reaching the receiver after 33 ms. To avoid overlap between original and reflected waves the pulse duration must be less than 6 ms. Using a 50 kHz carrier wave, a 6 ms pulse can transfer about 900 bits of binary data using on-off scheme, and 100 bits of binary data using DPIM.

While the use of a pulse transmission technique may eliminate interference between the original and reflected waves, it also causes the receiver to capture two identical waves at two different times. To avoid confusion, a transmission time can be included in every transmission. The receiver will check the transmission time of every received signal, and will ignore the signal if the transmission time is identical to a previous reception. Another method to avoid confusion associated with reflected waves is for the receiver to turn off the receiving circuit for a few hundred milliseconds after the complete data package is received.

PSK (Phase-shift Keying): PSK uses the phase of the carrier signal (generally a sinusoidal signal) to express binary information. For example, a signal with a phase of 0° represents a binary state of '0', while a signal with a phase of 180° means a binary '1'. PSK consumes more power than the OOK and DPIM because the transducer has to be turned on at all time regardless of the binary state. The nature of PSK makes the receiver circuitry necessary to implement PSK, more complex than that of the OOK and DPIM. In OOK and DPIM, demodulation of the signal may be accomplished by detecting the envelope of the signal; to operate the receiver does not required detailed information of the carrier signal itself. Whereas, in order to demodulate a PSK signal properly, the receiver must know the specific frequency and phase of the carrier from the transmitter, thus a PLL (Phase-Locked Loop) may be employed to extract the carrier's detailed information from the received signal.

FSK (Frequency-Shift Keying): FSK uses the frequency of the carrier signal to express binary information. For example, a carrier signal with frequency $f_1$ represents a binary '0'; another carrier signal with frequency $f_2$ represents a binary '1'. Similar to PSK, FSK consumes more power than the OOK and DPIM because the transducer has to be on at all time regardless of the binary state. As is the case using PSK, a PLL is required in the circuit of a FSK receiver.

Multi-Dimensional Modulation: The modulation techniques described above may be expanded to multi-dimensional domains. For example, the PSK can be expanded to Quadrature Phase Shift Keying (QPSK), the OOK to Quadrature Amplitude Modulation (QAM), and the FSK to Multiple Frequency Shift Keying (MFSK), and so on. In general, these multi-dimensional modulation schemes are similar to their two-dimensional counterpart. However, instead of modulating one bit at a time, the multi-dimensional modulation schemes take more than one bit at a time and modulate them. For example, in QPSK, every two bits of the binary data are combined and depending upon the value of the combined data, the two bits are represented by one of four carrier phases which are equally separated, for example, 0°, 90°, 180°, and 270°. Use of a multi-dimensional modulation technique can expand the channel capacity and support higher communication speed. However, to accomplish this they require complex circuitry and consume more power.

another sensor (active sensor 222) is coated with a chemically responsive layer intended for exposure to the analyte of interest. A fixed frequency voltage signal is passed through both sensors, and the chemical concentration determined from the measured amplitude and phase difference between the two sensors. The measured voltage and phase are sent to base, where the chemical concentration level may be determined from a pre-calibration lookup table, for example. As is shown for element 210, sensor element module 220 has an

TABLE A summarizes features of several modulation techniques:

| Modulation Method | DPIM-OOK | Common ASK | PSK | FSK | Multi-Dimension (QPSK, QAM, MFSK, etc) |
|---|---|---|---|---|---|
| demodulation method | Envelop detection | Envelop Detection or Coherent detection | Coherent detection (PLL needed) | Coherent detection (PLL needed) | Coherent detection (PLL needed) |
| relative Pwr Consumption | Lower | Higher | Higher | Higher | Higher |
| Relative comm speed | Lower | Lower | Lower | Lower | Higher |

FIG. 18 is a schematic diagram of an embodiment of sensor interface circuitry 180 adapted for interfacing potential-based sensor elements such as, by way of example only, a thermistor for measuring/sensing temperature of an environment. The output from the sensors is 'conditioned' before it can be digitized by the microcontroller for further processing. Sensor interface circuitry is tailored to use of different types of sensors. A multiplexer can be used to select each sensor at a time. FIG. 19 has isometric depictions of alternative sensor element assemblies, respectively labeled 190 (a temperature sensor/thermistor) and 192 (a pH sensor).

FIG. 20 is a schematic diagram of an embodiment of sensor interface circuitry 200 adapted for interfacing resistive-type sensor elements (e.g., at 220 in FIG. 22) for measuring/sensing parameters of an environment.

FIG. 21 is a top plan schematic view of a Surface Acoustic Wave (SAW) type sensor element 210 suitable for collecting information concerning liquid viscosity and density, concentration of an analyte of interest within the liquid environment. Components include: chemical sensitive material 211, SAW substrate 212, receiving IDT 213, access to node assembly communication (Comm) port 214, access to node output port 215, access to node input port 216, and transmitting IDT.

FIG. 22 is a top plan schematic view of an impedance sensor element (or resistive-type sensor) 220, such as that shown with an interdigital capacitor coated with a layer selected for its response to exposure to an analyte of interest within the liquid environment. Impedance sensors operate based on changes in electrical impedance—an example is the simple interdigital capacitor coated with chemically responsive layer at 220. The chemical concentrations are determined from the changes in the measured impedance, which are due to the changes in the electrical properties of the chemically responsive layer. The impedance sensor module 220 consists of two identical sensors in series, reference sensor 221 and active sensor 222. A non-permeable coating 227 is used to shield one sensors (the reference sensor 221), preventing the analyte from contacting it, while access to node assembly communication (Comm) port depicted at 224, access to node output port at 225, access to node input port at 226.

FIG. 23A is a top plan schematic view of a magnetoelastic-type sensor element 230 for use to monitor an analyte of interest within the liquid environment; magnetoelastic sensor elements are suitable for collecting a wide range of information about analytes as well as a variety of parameters of liquid and gas environments. FIG. 23B graphically depicts a pulse-modulated sinusoidal excitation signal and, beneath it, the sensor's response to having been exposed to the excitation signal—both of which are characteristic of operational features of the sensor in FIG. 23A. A magnetoelastic sensor element(s) 231 may be used to monitor chemical concentrations by applying a thin coating of a mass (or elasticity) changing chemically responsive material, and measuring the shift in resonant frequency or quality factor Q as a function of chemical concentration. The resonant frequency is detected by interrogating the sensor by a pulse-modulated sinusoidal magnetic field generated by a CPU of the module, and counting the frequency of the ac magnetic flux generated by the sensor after the excitation signal is turned off. The magnetoelastic sensor module 230 consists of an excitation loop 237 and detection/sensing loop 238. The magnetoelastic ribbon 231 is supported 232 at its center, the vibration null point, and a bias magnetic strip 233 is used to increase the sensor vibration by increasing the magnetostrictive effects of the sensor. The excitation loop 237 is connected to the output port 235 of the sensor node and the sensing loop 238 is connected to the input port 236 of the sensing node. Just as elements 210 and 220, element 230, likewise, has an access to node assembly communication (Comm) port (depicted at 234).

For further examples of the many and variety of suitable sensor elements that may be adapted for immersion in the liquid medium undergoing monitoring and incorporation within node assemblies (for reference, see FIGS. 3-6) at network node locations, please refer to the following published references also identified in applicants' pending provisional application: U.S. Pat. No. 6,393,921 B1 issued 28

May 2002 to Grimes et al. entitled "Magnetoelastic Sensing Apparatus and Method for Remote Pressure Query of an Environment;" U.S. Pat. No. 6,397,661 B1 issued 04 Jun. 2002 to Grimes et al. entitled "Remote Magneto-elastic Analyte, Viscosity and Temperature Sensing Apparatus and Associated Method of Sensing;" Reindl et al. "Theory and Application of Passive SAW Radio Transponders as Sensors," IEEE Transactions on Ultrasonics, Ferroelectrics, and Frequency Control, vol. 45, no. 5, (September 1998); Frye et al. "Optimizing Surface Acoustic Wave Sensors for Trace Chemical Detection," IEEE International Conference on Solid-state Sensors and Actuators, (1997) 1323-1326; Grimes, C. A., K. G. Ong, et al. "Magnetoelastic sensors for remote query environmental monitoring," Journal of Smart Materials and Structures, vol. 8 (1999) 639-646; and Jain, M. K., C. A. Grimes, "A Wireless Magnetoelastic Micro-Sensor Array for Simultaneous Measurement of Temperature and Pressure," IEEE Transactions on Magnetics, vol. 37, No. 4, pp. 2022-2024, 2001.

Figure 24:
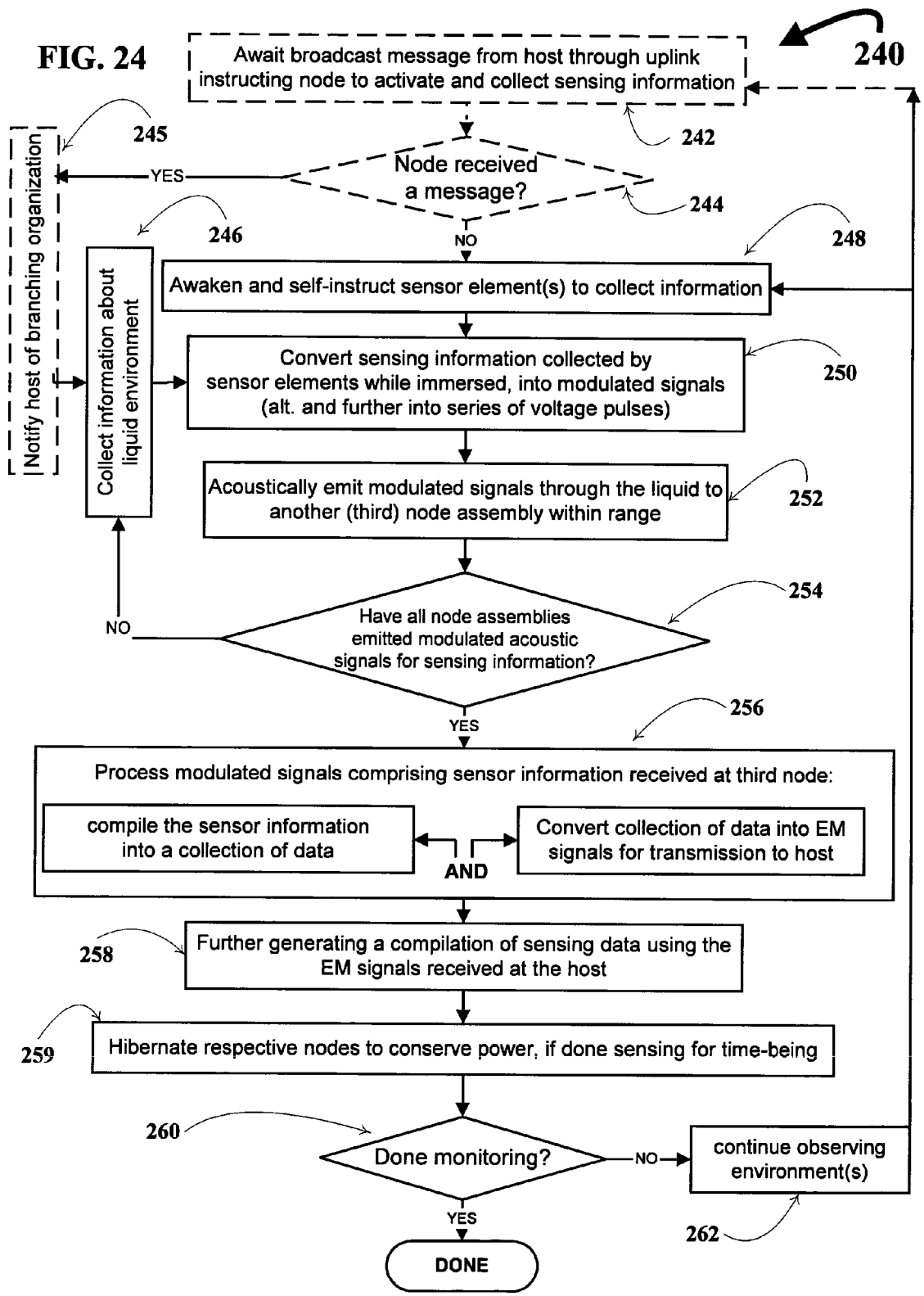
FIG. 24 is a flow diagram depicting details of a method 240 of transmitting information collected about a liquid environment utilizing a network comprising at least a first and second node assembly, according to the invention. Illustrated are core, as well as further distinguishing, features for transmitting information within the network such as the features represented and depicted in applicants' other FIGS.

FIG. 24 is a flow diagram depicting details of a method 240 of transmitting information collected about a liquid environment utilizing a network comprising at least a first and second node assembly, according to the invention. Illustrated in FIG. 24 are core, as well as further unique and distinguishing, features for transmitting information within the network such as the features represented and depicted in applicants' other figures. As explained throughout, sensing node assemblies dispersed for sensing an environment may be awakened by internal circuitry (box 248), for example turned on at selected intervals, and/or may await a broadcast message (box 244) from a central 'command' unit (box 242) to awaken and organize. By way of suitable branched hierarchy protocol, nodes can communicate with neighbors to establish groupings and subgroups, for which a parent is identified and send messages back (box 245) to an uplink assembly (FIG. 3, 32) or through the uplink and on to a host assembly location (FIGS. 1 and 3, 62, 62'). Sensing information collected about the environment (box 248 and box 246) may be converted into modulated signals and further into a series of voltage pulses (box 250) for acoustic emission through the liquid environment (box 252). A loop in flow diagram of method 240 depicts the example situation where certain of the assemblies that were requested to submit sensing information either via host message (box 242) or via internal timing circuitry (box 248) have not done so (254)—regardless of the reason, such as no message was received due to a glitch in the network, power has been consumed and the power source for that assembly needs to be replaced, the timing circuitry is non-operational, and so on. Whether an uplink type intermediary node is used within the network, the sensor information received by a third node (box 256) may be processed by compiling into a collection of sensing data (FIG. 3 at 37) and converting into signals for further transmission (FIG. 3 at 69 and/or 66) to a host location (FIGS. 1 and 3 at 62, 62'). The host further processes the data received (box 258 and FIG. 3 at 67) for use (FIGS. 2 and 3 at 64, 69) by a monitoring station, government agency, an individual collecting information about health of an environment, and so on. If not done monitoring, 260 the process may continue 262 as long as a sufficient number of network node assemblies are functional and capable of receiving and transmitting information via acoustic signals.

NETWORK EXAMPLE 7

The network of the invention may utilize a branched hierarchy protocol to structure effective node arrangement. Referencing FIGS. 1-3 and 24, one can appreciate that each node from which sensing information is collected from the liquid environment 11 and/or surrounding air (or other environment in proximity) should have at least a neighboring node located within the radius of its transmission range. This may be accomplished, for example, by either adding more sensor nodes in an area or increasing the transmission range of the sensor nodes. Initially a host node location, through an uplink, may broadcast an activation signal (box 244) that is transmitted acoustically to neighboring nodes. Upon receiving the activation signal, the nearby nodes remember the host node as a grandparent, and in turn send out activation signals to other nodes to identify parent(s) nodes, and so on. This process is repeated until each node in the network have been given the identities of their (grand) parents. During operation, all nodes within a (sub)group, relay the sensing information/data collected to their parent nodes. The relaying process is repeated until the data from all sensor nodes is uploaded to the host node (62, 62'). The host node computer (64) will download the data from the host node, process it (67) and then present (via any suitable interface 69) to user-client devices.

Returning to FIG. 2, a base station computer 64, may be hardwired or otherwise EM linked to uplink node assembly 32 through the air/water interface. Node 32 receives any message(s) from host, and in turn, broadcasts an activation signal on to the next two closest nodes, 42 and 12. Upon receiving the activation signal, nodes 42 and 12 recognize node 32 as a parent. Node 12, in turn sends out activation signals to an unnumbered node (1) and to node 22—thus, 12 becomes a parent to those two nodes, with node 32 as a (grand)parent. Similarly, node 22 sends out an activation signal and becomes the parent of outlying node 52 and another (unnumbered) outlying node. The advantage of establishing communication via broadcasting activation signals is that it allows the nodes to adjust to changes in the network arrangement. For example, if node 12 is removed or damaged, the communication link to its 'children' nodes will be cut off. However, during the next activation process, those nodes initially cut-off may reestablish links to the base through node location 3, for example. Hence the sensor network system will function as long as there is at least one node within the transmission range of the other nodes. After collecting response and/or information of all relayed sensor modules, individual nodes may combine the data they receive, into a package and send the data to a parent node. The package is continuously relayed until reaching the base node. A suitable computerized device 64 connected to the base node (62, 62') collects packages and, as needed, convert the sensor data (67) into the parameter of interest for presentation (interface 69).

Several EXAMPLES have been provided merely for purposes of further understanding the novel features of the invention as depicted in the various figures. While certain representative embodiments and details have been shown for the purpose of illustrating the invention, those skilled in the art will readily appreciate that various modifications, whether specifically or expressly identified herein, may be made to the representative embodiments without departing from the novel teachings or scope of this technical disclosure. Accordingly, all such modifications are contemplated hereby and intended to be included within the scope of the claims. Although the commonly employed preamble phrase "comprising the steps of" may be used herein in a method claim, Applicants do not intend to invoke 35 U.S.C. §112 ¶6. Furthermore, in any claim that is filed herewith or hereafter, any means-plus-function clause(s) used, or later found to be present, are intended to cover at least all structure(s) described herein as performing the recited function and not only structural equivalents but also equivalent structures.

What is claimed is:

1. A network of remote sensing node assemblies, each of which has a sensor element, the network comprising:
   (a) each of the sensor elements adapted for immersion within a liquid environment for sensing therewithin, a first and second of the sensing node assemblies to function, respectively, as a first and second parent node, each within an acoustic transmission range with at least one other of the sensing node assemblies;
   (b) each respective one of the node assemblies to comprise: a source of power for said respective node assembly; a transducer for receiving acoustic waves transmitted from a different one of the node assemblies while immersed within said liquid environment; acoustic-transducer circuitry for converting said acoustic waves received by said different node assemblies, into signals; a controller adapted for local processing of said signals within said respective node assembly; said transducer further adapted for emitting, for transmission through said liquid environment, sensor information collected about said liquid environment by the sensor element of said respective node assembly;
   (c) each said respective node assembly adapted for processing said sensor information collected about said liquid environment by the sensor element of said respective node assembly; and
   (d) a third one of the sensing node assemblies further adapted for transmitting said sensor information collected by said third node assembly to a remote host.

2. The network of claim 1 wherein: said local processing of said signals within said respective node assembly comprises converting said signals into modulated signals for said emitting by said transducer; said modulated signals are further converted into a series of voltage pulses representing an encoding of said signals; said acoustic-transducer circuitry is further adapted for amplifying said series of voltage pulses; and said transducer comprises a plurality of directional transducers.

3. The network of claim 1 wherein: said local processing of said signals within said respective node assembly comprises converting said signals into modulated signals for said emitting by said transducer; said acoustic-transducer circuitry is further adapted for converting said modulated signals, into a series of voltage pulses which are then amplified prior to said emitting by said transducer; and said transducer comprises an omni-directional transducer.

4. The network of claim 1 wherein:
   said third node assembly further comprises means for transmitting said sensor information to said remote host selected from the group consisting of a radio frequency (RF) wave transceiver, a fiber-optic cable, an infrared (IR) transceiver, an optical transceiver, a microwave transceiver, a connection through conductive media, and an assembly comprising a cable and a connector.

5. The network of claim 3 wherein:
   (a) said converting said signals into modulated signals comprises employing a technique selected from the group consisting of On-Off Keying, Digital Pulse Interval Modulation, Phase-shift Keying, Frequency-shift Keying, Amplitude-shift Keying, Quadrature Phase-shift Keying, Quadrature Amplitude Modulation, and Multiple Frequency-shift Keying;
   (b) and
   (c) said processing by said third node comprises convening said sensor information acoustically received thereby having been collected about said liquid environment by the sensor element of said respective node assemblies, into a collection of data about said liquid environment for said transmitting to said remote host.

6. The network of claim 1 wherein:
   (a) said third node assembly comprises means for transmitting said sensor information to said remote host selected from the group consisting of a radio frequency (RF) wave transceiver, a fiber-optic cable, an infrared (IR) transceiver, an optical transceiver, a microwave transceiver, a connection through conductive media, and an assembly comprising a cable and a connector; and
   (b) said host is adapted for communicating with a computerized device, said computerized device comprising an interface adapted for accessing said sensor information as a compilation of sensing data.

7. The network of claim 6 wherein:
   (a) said liquid environment is an aqueous body;
   (b) the first and second node assemblies are immersed in said aqueous body for said sensing;
   (c) and said means for transmitting said sensor information to said remote host is adapted for operation for said transmitting when not immersed in said aqueous body.

8. The network of claim 6 wherein:
   (a) said remote host comprises means for directly receiving said sensor information collected by said third node assembly and that collected by the sensor elements of other said respective node assemblies;
   (b) said computerized device is adapted for at least partially generating said compilation of sensing data;
   (c) said third node assembly is further adapted to, upon receiving instructions, transmitting a broadcast message to each said respective node assembly within an acoustic transmission range instructing a respective sensor element of said respective node assembly to perform said sensing; and
   (d) in response thereto, said sensor information is acoustically transmitted from each said respective node assembly having received said broadcast message, to said third node assembly for said third node processing.

9. The network of claim 6 wherein:
   (a) said each respective node assembly further comprises respective-node controller circuitry adapted for periodic activation of the sensor element of said respective node assembly to perform said sensing; upon perfonning said sensing, in the event a threshold value is exceeded, a node message is emitted from said transducer of said respective node assembly comprising said sensor information;
   (b) said third node assembly further adapted for converting any said node messages received for transmitting to said remote host; and
   (c) said remote host comprises means for receiving said converted node messages.

10. A network of remote sensing node assemblies, a first and second of which each has a sensor element, the network comprising:
   (a) each of the sensor elements adapted for immersion within a liquid environment for sensing therewithin;
   (b) each respective one of the first and second node assemblies to comprise: a source of power for said respective node assembly and a transducer for receiving acoustic waves transmitted from a different one of the node assemblies while immersed within said liquid environment, said transducer fUrther adapted for emitting, for transmission though said liquid environment, sensor information collected about said liquid environment by the sensor element of said respective node assembly;

(c) a third node assembly adapted for receiving and processing any said sensor information acoustically transmitted from said respective node assemblies;

(d) said third node assembly comprises means for transmitting said sensor information to a remote host;

(e) said each respective node assembly fUrther comprises respective-node controller circuitry adapted for periodic activation of the sensor element of said respective node assembly to perform said sensing; upon performing said sensing, in the event a threshold value is exceeded, a node message is emitted from said transducer of said respective node assembly comprising said sensor information; and (f) upon receiving any said node message, an alert-type message is generated for transmission by said remote host to said third node assembly instructing said respective node assemblies to decrease an interval time between each successive of said periodic activation.

* * * * *